(12) United States Patent
Liu et al.

(10) Patent No.: US 11,020,075 B2
(45) Date of Patent: *Jun. 1, 2021

(54) IMPLANTATION OF AN ACTIVE MEDICAL DEVICE USING THE INTERNAL THORACIC VASCULATURE

(71) Applicant: CARDIAC PACEMAKERS, INC., St. Paul, MN (US)

(72) Inventors: Lili Liu, Maple Grove, MN (US); Andrew L. De Kock, Ham Lake, MN (US); James O. Gilkerson, Stillwater, MN (US); James K. Cawthra, Jr., Ramsey, MN (US); G. Shantanu Reddy, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 500 days.

This patent is subject to a terminal disclaimer.

(21) Appl. No.: 15/976,078

(22) Filed: May 10, 2018

(65) Prior Publication Data

US 2018/0325480 A1  Nov. 15, 2018

Related U.S. Application Data

(60) Provisional application No. 62/505,388, filed on May 12, 2017.

(51) Int. Cl.
*A61B 6/00* (2006.01)
*A61N 1/05* (2006.01)
(Continued)

(52) U.S. Cl.
CPC .............. *A61B 6/481* (2013.01); *A61B 6/504* (2013.01); *A61B 90/37* (2016.02); *A61M 25/10* (2013.01);
(Continued)

(58) Field of Classification Search
CPC ...... A61B 2090/376; A61B 2090/3966; A61B 6/12; A61B 6/481; A61B 6/487;
(Continued)

(56) References Cited

U.S. PATENT DOCUMENTS 5,188,619 A    2/1993 Myers
5,331,966 A    7/1994 Bennett et al.
(Continued)

FOREIGN PATENT DOCUMENTS

WO    9219307 A1    11/1992
WO    2016148928 A1    9/2016
WO    2016149262 A1    9/2016

OTHER PUBLICATIONS

Advisory Action Before the Filing of an Appeal Brief for U.S. Appl. No. 15/667,167, dated Mar. 21, 2019.
(Continued)

*Primary Examiner* — Amelie R Davis
(74) *Attorney, Agent, or Firm* — Seager, Tufte & Wickhem LLP

(57) ABSTRACT

Implantation of a cardiac stimulus system using an illuminating catheter system, and devices for such implantation. Multiple catheter systems for allowing for selective visualization of the internal thoracic vasculature are discussed and disclosed. A multiple lumen catheter may be used to selectively direct a contrast agent to a desired portion of the thoracic vasculature which may include the internal thoracic vein(s) and/or one or more intercostal veins.

20 Claims, 12 Drawing Sheets

(51) Int. Cl.
- *A61B 90/00* (2016.01)
- *A61M 25/10* (2013.01)
- *A61N 1/375* (2006.01)
- *A61N 1/39* (2006.01)
- *A61B 6/12* (2006.01)
- *A61M 25/00* (2006.01)

(52) U.S. Cl.
CPC .............. *A61N 1/0563* (2013.01); *A61B 6/12* (2013.01); *A61B 2090/376* (2016.02); *A61B 2090/3966* (2016.02); *A61M 2025/0037* (2013.01); *A61M 2025/0039* (2013.01); *A61N 1/3756* (2013.01); *A61N 1/3962* (2013.01)

(58) Field of Classification Search
CPC .................. A61B 6/504; A61B 90/37; A61M 2025/0037; A61M 2025/0039; A61M 25/10; A61N 1/0563; A61N 1/3756; A61N 1/3962
See application file for complete search history.

(56) References Cited

U.S. PATENT DOCUMENTS

| | | |
|---|---|---|
| 5,755,687 A | 5/1998 | Donlon |
| 6,647,292 B1 | 11/2003 | Bardy et al. |
| 6,721,597 B1 | 4/2004 | Bardy et al. |
| 6,836,687 B2 | 12/2004 | Kelley et al. |
| 7,149,575 B2 | 12/2006 | Ostroff et al. |
| 7,655,014 B2 | 2/2010 | Ko et al. |
| 7,783,340 B2 | 8/2010 | Sanghera et al. |
| 7,818,068 B2 | 10/2010 | Meadows et al. |
| 7,935,075 B2 | 5/2011 | Tockman et al. |
| 7,962,222 B2 | 6/2011 | He et al. |
| 8,005,543 B2 | 8/2011 | Libbus et al. |
| 8,157,813 B2 | 4/2012 | Ko et al. |
| 8,386,048 B2 | 2/2013 | McClure et al. |
| 8,483,843 B2 | 7/2013 | Sanghera et al. |
| 8,543,216 B2 | 9/2013 | Carbunaru et al. |
| 9,492,658 B2 | 11/2016 | Shireman et al. |
| 2002/0026145 A1 | 2/2002 | Bagaoisan et al. |
| 2005/0043765 A1 | 2/2005 | Williams et al. |
| 2012/0029335 A1 | 2/2012 | Sudam et al. |
| 2014/0114371 A1 | 4/2014 | Westlund et al. |
| 2014/0135789 A1* | 5/2014 | Shireman ............... A61N 1/056 606/129 |
| 2014/0330326 A1 | 11/2014 | Thompson-Nauman et al. |
| 2015/0025612 A1 | 1/2015 | Haasl et al. |
| 2015/0051610 A1 | 2/2015 | Schmidt et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0224320 A1 | 8/2015 | Stahmann |
| 2015/0297902 A1 | 10/2015 | Stahmann et al. |
| 2015/0360036 A1 | 12/2015 | Kane et al. |
| 2016/0038742 A1 | 2/2016 | Stahmann et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0228712 A1 | 8/2016 | Koop |
| 2016/0256692 A1 | 9/2016 | Baru |
| 2017/0021159 A1 | 1/2017 | Reddy et al. |
| 2017/0095657 A1 | 4/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2018/0036527 A1 | 2/2018 | Reddy et al. |
| 2018/0036547 A1 | 2/2018 | Reddy |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0178018 A1 | 6/2018 | Reddy et al. |
| 2018/0178019 A1 | 6/2018 | Reddy et al. |
| 2018/0193060 A1 | 7/2018 | Reddy et al. |
| 2018/0214686 A1 | 8/2018 | De Kock et al. |
| 2018/0256890 A1 | 9/2018 | Fuhs et al. |
| 2018/0264270 A1 | 9/2018 | Koop et al. |
| 2018/0296824 A1 | 10/2018 | De Krock et al. |
| 2018/0325480 A1 | 11/2018 | Liu et al. |
| 2018/0344200 A1 | 11/2018 | Thakur et al. |
| 2018/0344252 A1 | 11/2018 | An et al. |

OTHER PUBLICATIONS

Final Office Action for U.S. Appl. No. 15/667,167, dated Jan. 10, 2019.
Non-Final Office Action for U.S. Appl. No. 15/667,167, dated Jun. 26, 2018.
Non-Final Office Action for U.S. Appl. No. 15/667,167, dated Aug. 7, 2019.
Final Office Action for U.S. Appl. No. 15/667,221, dated Apr. 11, 2019.
Non-Final Office Action for U.S. Appl. No. 15/667,221, dated Oct. 1, 2018.
Notice of Allowance and Fees Due for U.S. Appl. No. 15/667,221, dated Jul. 11, 2019.
Amendment for U.S. Appl. No. 15/667,167, dated Sep. 17, 2018.
Amendment for U.S. Appl. No. 15/667,167, dated Oct. 9, 2019.
Amendment After Final Office Action for U.S. Appl. No. 15/667,167, dated Mar. 11, 2019.
Request for Continued Examination (RCE) for U.S. Appl. No. 15/667,167, dated Apr. 10, 2019.
Amendment for U.S. Appl. No. 15/667,221, dated Dec. 21, 2018.
Amendment After Final Office Action for U.S. Appl. No. 15/667,221, dated May 22, 2019.
Moenipour et al., "A Rare Central Venous Catheter Malposition: A Case Report," Anesth Pain Med., 4(1): 1-3, Feb. 5, 2014.
Schuder et al., "Experimental Ventricular Defibrillation with and Automatic and Completely Implanted System," Trans. Amer. Soc. Artif. Int. Organs, XVI: 207-212, 1970.
Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.
Ghosh et al., "A Rare Malposition of the Thoracic Venous Catheter Introduced via the Left Internal Jugular Vein," Indian J. Crit. Care Med., 12(4): 201-203, Oct.-Dec. 2008.
Loukas et al., "The Clinical Anatomy of the Internal Thoracic Veins," Folia Morphol, 66(1): 25-32, 2007.
International Search Report and Written Opinion dated Sep. 29, 2017 for International Application No. PCT/US2017/045109.
"Angiography Catheter," Cardiomed Life-Sustaining Solutions, Jan. 11, 2018.

* cited by examiner

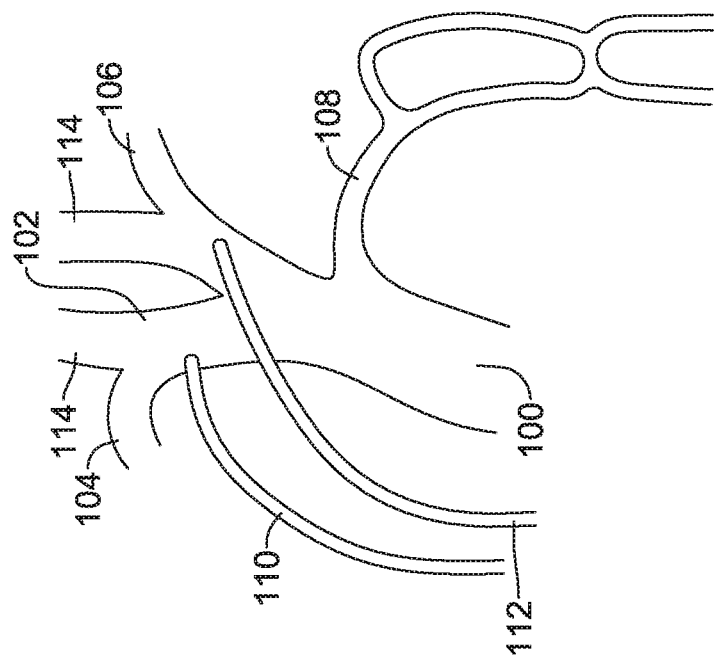
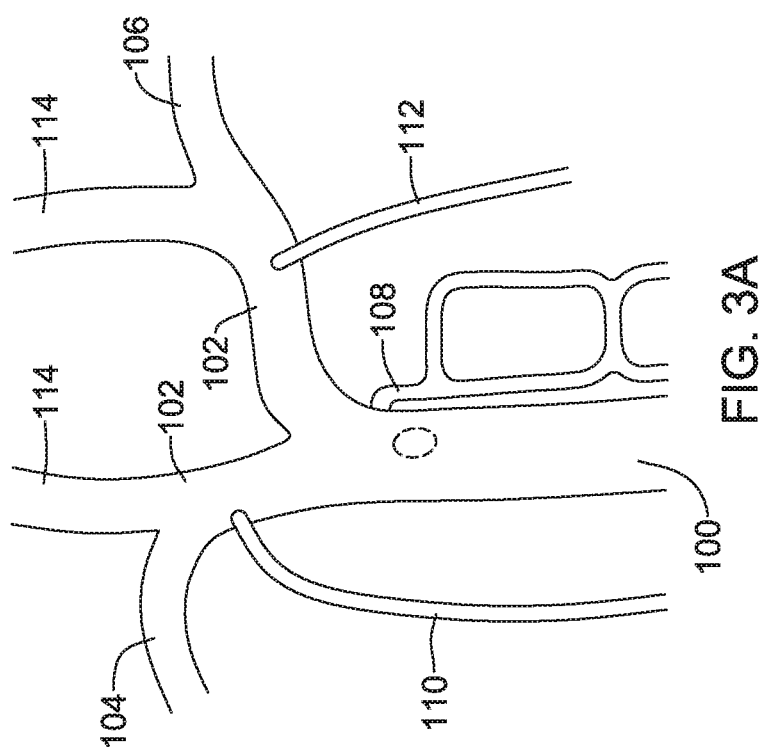

IMPLANTATION OF AN ACTIVE MEDICAL DEVICE USING THE INTERNAL THORACIC VASCULATURE

CROSS REFERENCE TO RELATED APPLICATIONS

The present application claims the benefit of and priority to U.S. Provisional Patent Application Ser. No. 62/505,388, filed on May 12, 2017 and titled IMPLANTATION OF AN ACTIVE MEDICAL DEVICE USING THE INTERNAL THORACIC VASCULATURE, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding the thoracotomy and improving reliability. However, lead failure remained a significant issue, as the lead attachment in the heart cause the lead to flex with each heartbeat. The advent of subcutaneous defibrillators allows avoidance of these lead failure issues, with leads implanted beneath the skin and over the ribcage of the patient and not subjected to the repeated flexing.

However, subcutaneous defibrillators require higher energy for defibrillation, causing the pulse generators for such systems to be larger than their transvenous predecessors, and both bradycardia pacing and anti-tachycardia pacing to avoid high voltage shock for certain conditions is of limited utility, because such pacing subcutaneously can be very uncomfortable for the patient. This has led to interest in further alternative locations for implantable defibrillators, and other medical devices such as the implantable pacemaker.

OVERVIEW

The present inventors have recognized, among other things that the internal thoracic vasculature including, in particular, the internal thoracic vein (ITV), sometimes also referred to as the internal mammary vein, presents an opportunity for an additional alternative implant location or access to alternative implant locations. A lead for an implantable cardiac device may be implanted into one or both ITVs. Alternatively or additionally, a lead may be implanted in an intercostal vein. Intercostal veins may also be used to extend laterally along the chest wall and even to the posterior of the patient, accessing the azygos, hemiazygos, or accessory hemiazygos veins if desired. Implantation to these locations may be made easier by performing steps to visualize the vasculature prior to implant. For example, the locations of access to blood vessels may be visualized, and the size of the vessels may be estimated to allow selection of appropriate lead sizing/design, access point, and routes of implantation, as further described below.

In a first example, a catheter may comprise an elongate shaft having a proximal end region and a distal end region. The distal end region may include a distal tip for advancement in a blood vessel of a patient and the shaft may include a plurality of lumens extending from the proximal end region to the distal end region. A first inflatable balloon may be coupled to the elongate shaft and in fluid communication with a first lumen of the plurality of lumens. A first port may be positioned at a distal end of the elongate shaft, the first port distal to the first inflatable balloon and in fluid communication with a second lumen of the plurality of lumens. A second port may extend through a side wall of the elongate shaft, the second port proximal to the first inflatable balloon and in fluid communication with a third lumen of the plurality of lumens. A hub assembly may be affixed to the elongate shaft adjacent to the proximal end region of the elongate shaft.

Alternatively or additionally to any of the examples above, in another example, the catheter may further comprise a second inflatable balloon coupled to the elongate shaft proximal to the first inflatable balloon and in fluid communication with the first lumen of the plurality of lumens and the second port may be distal to the second inflatable balloon.

Alternatively or additionally to any of the examples above, in another example, the hub assembly may comprise a Luer valve.

Alternatively or additionally to any of the examples above, in another example, the Luer valve may be in fluid communication with the first lumen.

Alternatively or additionally to any of the examples above, in another example, the hub assembly may comprise a first injection port.

Alternatively or additionally to any of the examples above, in another example, the first injection port may be in fluid communication with the second lumen.

Alternatively or additionally to any of the examples above, in another example, the hub assembly may comprise a second injection port.

Alternatively or additionally to any of the examples above, in another example, the second injection port may be in fluid communication with the third lumen.

Alternatively or additionally to any of the examples above, in another example, the catheter may further comprise a third port extending through a side wall of the elongate shaft, the third port may be proximal to the second inflatable balloon and in fluid communication with a fourth lumen of the plurality of lumens.

Alternatively or additionally to any of the examples above, in another example, the hub assembly may comprise a third injection port.

Alternatively or additionally to any of the examples above, in another example, the third injection port may be in fluid communication with the fourth lumen.

Alternatively or additionally to any of the examples above, in another example, the catheter may have a length in the range of about 30 to 50 centimeters.

Alternatively or additionally to any of the examples above, in another example, the elongate shaft may have a length in the range of about 20 to 40 centimeters.

In another example, a method for identifying a vein for implanting a lead for use in a cardiac stimulus system in a patient, the lead having at least one electrode thereon may comprise locating a selected musculophrenic or superior epigastric vein, establishing access to the selected vein, introducing the catheter of any one of the examples above into the selected vein, and injecting a contrast agent through the catheter; and taking a first venography.

In another example, a method of implanting a lead for use in a cardiac stimulus system in a patient, the lead having at least one electrode thereon may comprise performing the method of any of the above examples to identify a target vein and inserting the lead into the target vein to a desired location relative to a heart of a patient.

In another example, a method for identifying a vein for implanting a lead for use in a cardiac stimulus system in a patient, the lead having at least one electrode thereon may comprise locating a selected musculophrenic or superior epigastric vein, establishing access to the selected vein, introducing the catheter of any one of the examples above into the selected vein, and injecting a contrast agent through the catheter; and taking a first venography.

Alternatively or additionally to any of the examples above, in another example, the catheter may comprise an elongate shaft having a proximal end region and a distal end region. The elongate shaft may comprise a plurality of lumens extending from the proximal end region to the distal end region. A first inflatable balloon may be coupled to the elongate shaft and in fluid communication with a first lumen of the plurality of lumens. A first port may be positioned at a distal end of the elongate shaft, the first port distal to the first inflatable balloon and in fluid communication with a second lumen of the plurality of lumens. A second port may extend through a side wall of the elongate shaft, the second port proximal to the first inflatable balloon and in fluid communication with a third lumen of the plurality of lumens. A hub assembly may be affixed to the elongate shaft adjacent to the proximal end region of the elongate shaft.

Alternatively or additionally to any of the examples above, in another example, the catheter may further comprise a second inflatable balloon coupled to the elongate shaft proximal to the first inflatable balloon and in fluid communication with the first lumen of the plurality of lumens and wherein the second port may be distal to the second inflatable balloon.

Alternatively or additionally to any of the examples above, in another example, the catheter may have a length in the range of about 30 to 50 centimeters.

Alternatively or additionally to any of the examples above, in another example, the elongate shaft may have a length in the range of about 20 to 40 centimeters Alternatively or additionally to any of the examples above, in another example, the hub assembly may comprise a first injection port.

Alternatively or additionally to any of the examples above, in another example, the first injection port may be in fluid communication with the second lumen.

Alternatively or additionally to any of the examples above, in another example, the hub assembly may comprise a second injection port.

Alternatively or additionally to any of the examples above, in another example, the second injection port may be in fluid communication with the third lumen Alternatively or additionally to any of the examples above, in another example, a third port may extend through a side wall of the elongate shaft, the third port proximal to the second inflatable balloon and in fluid communication with a fourth lumen of the plurality of lumens.

Alternatively or additionally to any of the examples above, in another example, the hub assembly may comprise a third injection port.

Alternatively or additionally to any of the examples above, in another example, the third injection port may be in fluid communication with the fourth lumen.

Alternatively or additionally to any of the examples above, in another example, an implant location may be chosen based on a size of a vein.

In another example, a method of implanting a lead for use in a cardiac stimulus system in a patient, the lead having at least one electrode thereon may comprise performing the method of any of the above examples to identify a target vein and inserting the lead into the target vein to a desired location relative to a heart of a patient.

Alternatively or additionally to any of the examples above, in another example, the target vein may be an internal thoracic vein.

Alternatively or additionally to any of the examples above, in another example, the target vein may be an intercostal vein.

Alternatively or additionally to any of the examples above, in another example, the target vein may be selected from the group consisting of the azygos vein, the hemiazygos vein, and the accessory hemiazygos vein.

In another example, a method for identifying a vein for implanting a lead for use in a cardiac stimulus system in a patient, the lead having at least one electrode thereon may comprise locating a selected musculophrenic or superior epigastric vein, establishing access to the selected vein, introducing a catheter into the selected vein, injecting a contrast agent through the catheter at a first location in the patient, taking a first venography, injecting a contrast agent through the catheter at a second location in the patient, and taking a second venography.

Alternatively or additionally to any of the examples above, in another example, the first location in the patient may be adjacent to a first injection port in the catheter and the second location in the patient may be adjacent to a second injection port in the catheter.

Alternatively or additionally to any of the examples above, in another example, the catheter may be repositioned within the patient prior to injection the contrast agent at the second location in the patient.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3a and 3b show the ITVs and linked vasculature in isolation;

DETAILED DESCRIPTION

Figure 1A:
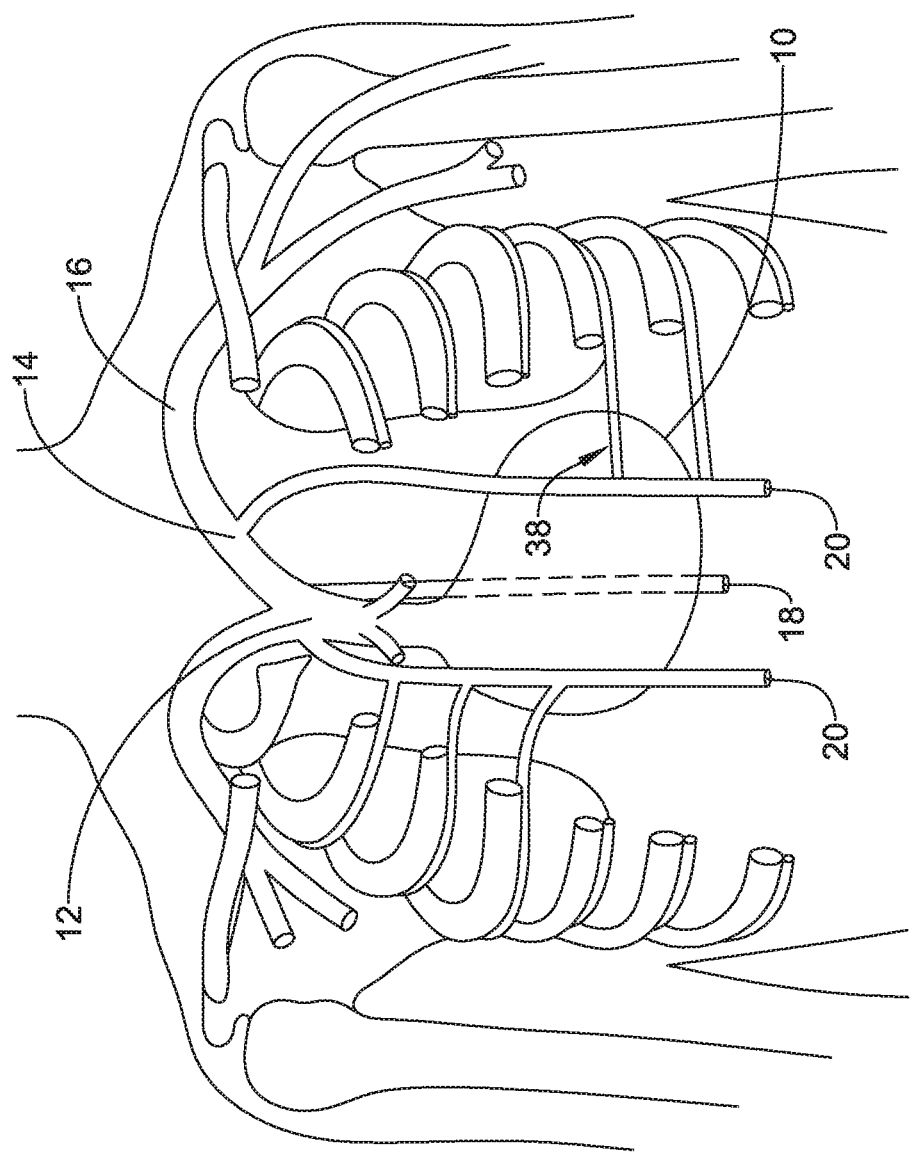
FIG. 1a illustrates the thoracic anatomy including placement of the internal thoracic veins (ITVs)

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUB-CUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate select fast tachycardias, have created interest in alternative defibrillator and/or pacemaker placement techniques. One proposal has included a substernal placement, with a lead extending beneath the sternum from a position inferior to the lower rib margin, such as in U.S. patent application Ser. No. 15/208,682, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

The present inventors have identified still a further alternative. In human anatomy, the internal thoracic vein (ITV), which may also be referred to as the internal mammary vein, is a vessel that drains the chest wall and breasts. There are both left and right internal thoracic veins on either side of the sternum, beneath the ribs. The ITV arises from the superior epigastric vein and musculophrenic vein, accompanies the internal thoracic artery along its course and terminates in the brachiocephalic vein. The inventors have recognized that the ITV may make a suitable location for placement of a cardiac stimulus lead. Additionally or alternatively, a lead may be placed in an intercostal vein, as described in more detail herein. The intercostal veins are veins that drain the rib cage's intercostal spaces. Anterior intercostal veins drain the anterior intercostal space into the internal thoracic veins while posterior intercostal veins drain into the azygos system of veins. While much of the following disclosure focuses on the use of the ITV, the intercostal veins, and/or veins connected to the ITV and/or intercostal veins many of these concepts could also be applied to the internal thoracic arteries, intercostal arteries and/or arteries connected to the internal thoracic arteries or intercostal arteries, which may sometimes be referenced as the internal mammary arteries.

FIG. 1A illustrates the thoracic anatomy including location of the internal thoracic veins (ITVs). An outline of the heart is shown at 10, with the superior vena cava (SVC) shown at 12. The brachiocephalic veins 14 couple to the SVC and extend past various cephalic branches to the subclavian vein 16. The azygos vein is shown at 18, and the right and left ITV are shown 20. The intercostal veins 38 run along the inferior margin of the several ribs, and drain into the ITV 20 as illustrated.

As used herein, the "ITV" is the name applied for the vein while it runs beneath the chest, that is, superior to the lower margin of the ribs. Inferior to the lower margin of the ribs, the blood vessel continues as the superior epigastric vein. At the lower margin of the ribs, the superior epigastric vein meets the musculophrenic vein, and superior to that union the vessel may be considered the ITV for purposes herein.

Figure 1B:
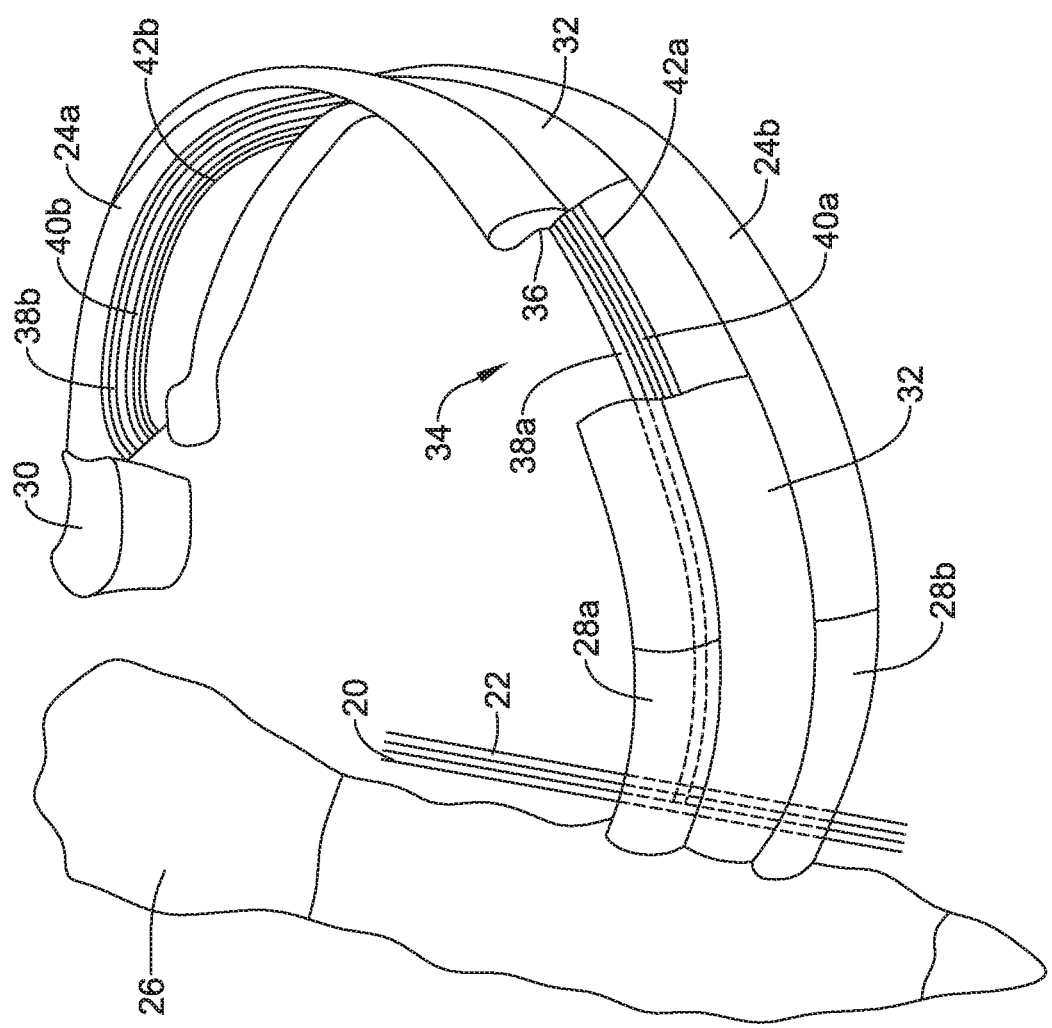
FIG. 1b illustrates the a close up view of a portion of the thoracic anatomy including placement of the ITVs and the intercostal veins.

FIG. 1B illustrates an alternative view of some of the left thoracic anatomy. The ribs 24a, 24b (collectively, 24) are connected anteriorly to the sternum 26 through costal cartilage 28a, 28b (collectively, 28) and are coupled posteriorly to the spine 30. It should be understood that for clarity, not all of the ribs 24, or other anatomy that may be present, are illustrated. Intercostal muscle 32 extends between the ribs 24. A region of one of the ribs 24a, and a portion of the intercostal muscle 32 has been removed at the area generally indicated by arrow 34 to expose the anterior intercostal vein 38a, the anterior intercostal artery 40a, and the anterior intercostal nerve 42a disposed in or adjacent to the costal groove 36. Each rib in the ribcage includes an intercostal vein, artery, and nerve.

The anterior intercostal vein 38a follows the rib 24a laterally and posteriorly to become the posterior intercostal vein 38b. Similarly, the anterior intercostal artery 40a and the anterior intercostal nerve 42a follow the rib 24a laterally and posteriorly to become the posterior intercostal artery 40b and the posterior intercostal nerve 40b, respectively. The left anterior intercostal veins 38a drain to the left ITV 20, shown next to the internal thoracic artery 22. The anterior intercostal vein 38a is shown in phantom under the rib 24a to further illustrate this connection between the ITV 20 and the anterior intercostal vein 38a. While not explicitly shown, the right anterior intercostal veins drain to the right ITV. The posterior intercostal veins 38b drain to the azygos vein system. The superior left posterior intercostal veins drain to the accessory hemiazygos vein, the inferior left posterior intercostal veins drain to the hemiazygos vein and the right posterior intercostal veins drain to the azygos vein.

Figure 2:
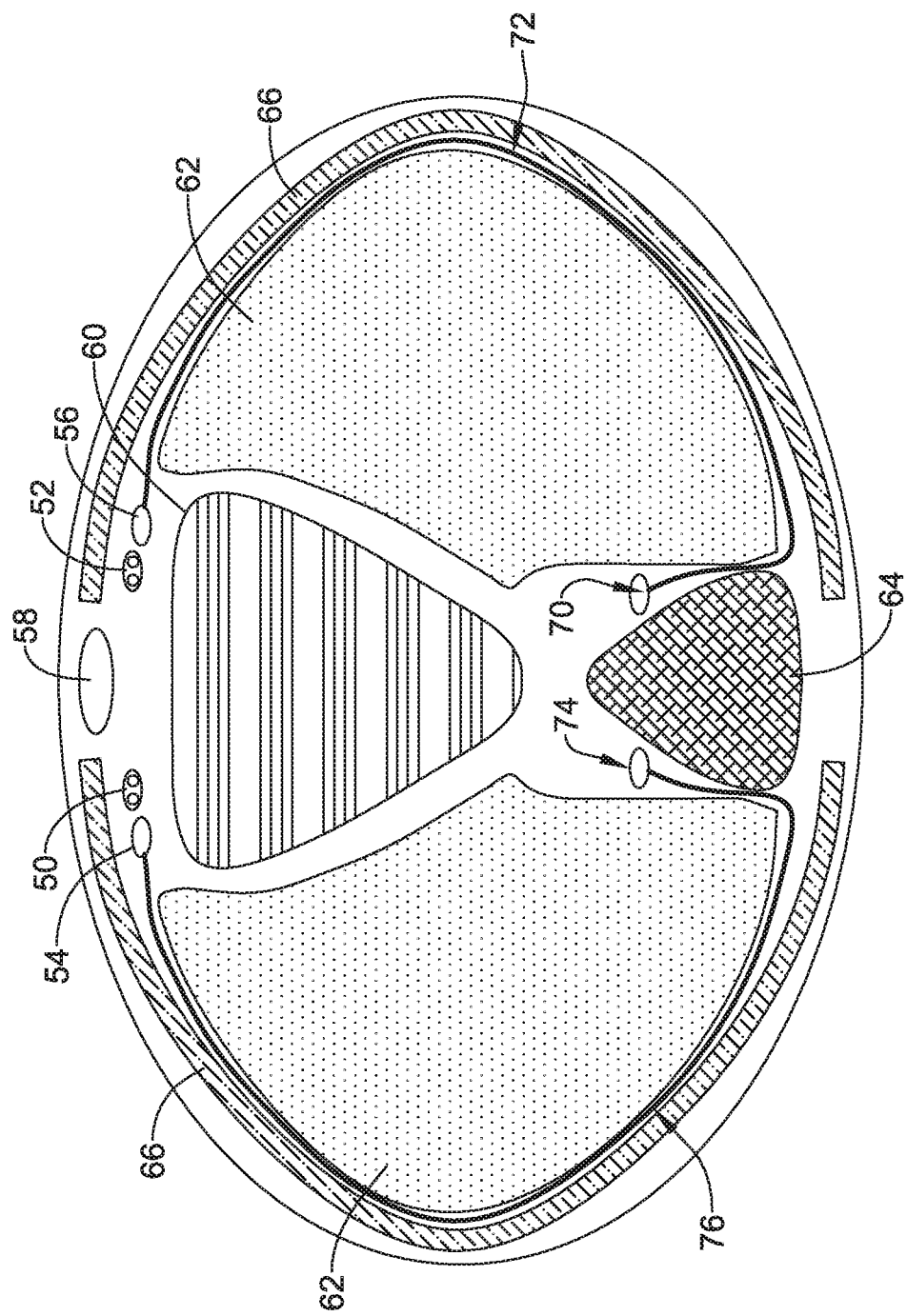
FIG. 2 shows the torso in a section view to highlight the location of the ITVs and arteries.

FIG. 2 shows the torso in a section view to highlight the location of the ITVs and internal thoracic arteries. More particularly, in the example, the left and right ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs 66 but outside and separate from the pleurae of lungs 62. On the right side of the patient's spine is the azygos vein 70, which is linked by the right intercostal veins 72 to the right ITV 52. On the left side of the patient spine is the hemiazygos vein 74, which is linked by the left intercostal veins 76 to the left ITV 50. At a position more superior on the patient, vessel 74 would instead be the accessory hemiazygos vein.

The relatively superficial position makes the ITV 50, 52 accessible percutaneously inferior to the rib margin or through intercostal spaces between ribs 66 as further discussed below. Access to the ITV from an access point inferior to the lower rib margin may be described as accessing the ITV via the superior epigastric vein. In some examples, the ITV may be accessed by first accessing the musculophrenic vein at the lower rib margin. Also shown in some examples below are methods to access to the ITV via the superior vasculature, including the brachiocephalic vein.

FIGS. 3A-3B show the ITV and linked vasculature in isolation. FIG. 3A is an anterior view of selected portions of the venous structure of the upper torso, and FIG. 3B is a lateral view of the same. The SVC is shown at 100, with the brachiocephalic veins 102 splitting at the upper end of the SVC. The right subclavian vein is at 104, and the left subclavian vein is at 106. The azygos vein is included in the illustration at 108, extending off the posterior of the SVC, and runs inferiorly posterior of the heart as can be understood from the lateral view of FIG. 3B. The right and left ITV are shown at 110, 112. These each branch off at a location that is considered part of the brachiocephalic veins 102. The internal jugular veins are also shown at 114.

The size of the left and/or right ITV may vary from patient to patient and along a length of the ITV. For example, in some cases the right ITV may have an outer diameter in in the range of 3 to 5 millimeters (mm) near the fourth rib and an outer diameter in the range of 2 to 3.5 mm near the xiphoid. In some cases, the left ITV may have an outer diameter in the range of 2.5 to 3.5 mm near the fourth rib and an outer diameter in the range of 2.8 to 3.2 mm near the xiphoid. In some cases, ultrasound maybe be used to locate the ITV, but may not be sufficient to locate all portions thereof or to determine the size of the veins. It may be desirable to selectively distribute contrast to allow for the visualization of the ITV, the musculophrenic and/or superior epigastric vein, and/or the intercostal veins. This may allow the clinician to choose an appropriate vein and/or lead for lead placement.

Some examples and discussion of lead implantation using the ITV may be found in US PG Patent application Ser. Pub. No. 20180036527, titled IMPLANTATION OF AN ACTIVE MEDICAL DEVICE USING THE INTERNAL THORACIC VASCULATURE, and U.S. patent application Ser. No. 15/868,799, titled IMPLANTATION OF AN ACTIVE MEDICAL DEVICE USING THE INTERNAL THORACIC VASCULATURE, the disclosures of which are incorporated herein by reference.

Figure 4:
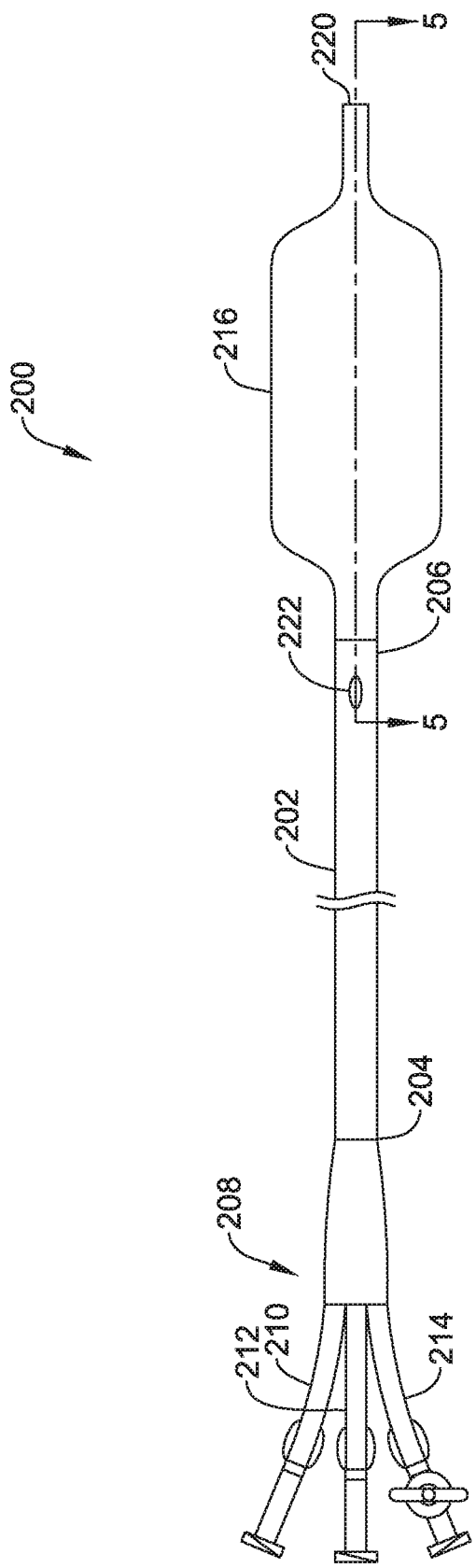
FIG. 4 shows a side view of an illustrative illuminating catheter for use in implantation of a lead.
Figure 5:
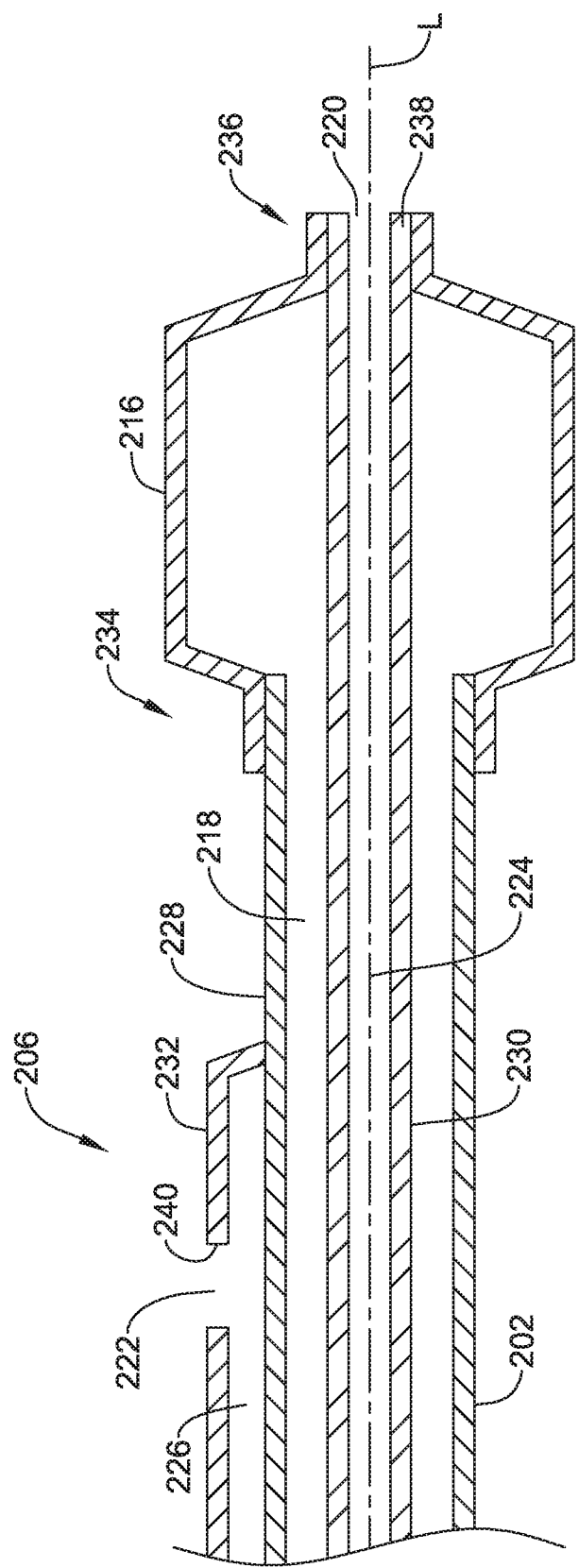
FIG. 5 shows a cross-sectional view of a distal portion of the illustrative catheter of FIG. 4, taken at line 5-5.

FIG. 4 shows side view of an illustrative catheter 200 which may be used to selectively illuminate the ITV and/or vasculature connected thereto. FIG. 5 illustrates a cross-sectional view of a distal portion of the catheter of FIG. 4, taken at line 5-5. The catheter 200 may be sized in length and diameter to reach the desired treatment region. For example, a 6 French (F) catheter may be used to access the ITV while a 3 F catheter may be required to access the intercostal veins. The balloon catheter 200 may include an elongate shaft 202 extending from a proximal end region 204 to a distal end region 206. In some examples particularly suited for access using the superior epigastric vein and/or the musculophrenic vein, the catheter 200 may have a length in the range of about up to 60 centimeters. In another example, the catheter 200 may have a total length in the range of about 30 to about 50 centimeters, with the shaft 202 extending from its proximal end for a length of about 20 to about 40 centimeters. The use of a shorter length may assist in inflation and deflation times, as the inflation fluid can more readily flow at lower pressures through the shorter catheter length. In other examples, the catheter may be longer, even as long as conventional angiography catheters in the range of 120 centimeters or so.

The catheter 200 may include a hub assembly 208 configured to remain outside of the body positioned adjacent to the proximal end 204 of the elongate shaft 202. In some instances, the hub assembly 208 may include a first contrast injection port 210, a second contrast injection port 212 and/or a Luer valve 214. It is contemplated that the hub assembly 208 may include fewer than three ports or more than three ports as desired. For example, the hub assembly 208 may include one, two, three, four, or more ports as desired.

The catheter 200 may include an inflatable balloon 216 positioned adjacent to the distal end region 206 of the elongate shaft 202. The balloon 216 may be in fluid communication with a first lumen or an inflation lumen 218 (shown in FIG. 5) which is in fluid communication with the Luer valve 214. The balloon 218 may be advanced through the vasculature in a collapsed or deflated state (not explicitly shown) and expanded or inflated once a target location has been reached. As will be described in more detail herein, the balloon 216 may be inflated to block or otherwise direct the flow of a contrast agent. For example, a proximal portion of the balloon 216 may be generally planar and configured to extend generally perpendicular to the longitudinal axis L of the catheter 200. In some cases, the balloon 216 may have a cone-like shape with the taper or point extending in the distal direction. The flat proximal surface may redirect contrast flow in a direction proximal to the balloon. It is contemplated that other balloon shapes may be used as desired to be control the flow of contrast, as desired.

The catheter 200 may further include a first contrast port or opening 220 positioned distal to the balloon 216 and a second contrast port or opening 222 positioned distal to the balloon 216. The first contrast port 220 is in fluid communication with a second lumen 224 which is in fluid communication with the first injection port 210. The second contrast port 222 is in fluid communication with a third lumen 226 which is in fluid communication with the second injection port 212.

The first lumen 218, the second lumen 224, and the third lumen 226 may extend within or otherwise be a part of the elongate shaft 202. In some embodiments, the elongate shaft 202 may be an extruded multi-lumen shaft 202. In other embodiments, the elongate shaft 202 may be formed from a plurality of individual tubes, each defining a lumen, which have been laminated, or otherwise bonded, together. It is further contemplated that the lumens 218, 224, 226 may be arranged in any manner desired, including but not limited to, coaxially, concentric, side by side, combinations thereof, etc.

In the illustrated embodiment, the elongate shaft 202 includes an intermediate tubular member 228 and an inner tubular member 230. The intermediate tubular member 228 extends from the proximal region 204 to a proximal portion of the balloon 216. The balloon 216 has a proximal portion 234 and a distal portion 236. The proximal portion 234 is bonded to the outer tubular member 228 of the shaft 202 and the distal portion 236 of the balloon 216 is bonded to the inner tubular member 230. The outer tubular member 228 defines a first lumen 218 for inflating the balloon 216. The inner tubular member 230 extends from the proximal region 204 of the elongate shaft 202 and through the distal end region 206 of the elongate shaft 202. The inner tubular member 230 defines the second lumen 224 that extends through the elongate shaft 202. An outer tubular member 232 may be positioned at a circumferential point extending along an outer surface of the intermediate tubular member 228 or surrounding (e.g., coaxially or eccentrically) the intermediate tubular member 228, as desired. The outer tubular member 232 defines the third lumen 226 that extends through the elongate shaft 202.

The inner tubular member 230 may terminate in an open distal end 238 defining the first contrast port 220. It is contemplated that fluid exiting through the first contrast port 220 will generally flow in line with a longitudinal axis of the catheter 200. While the open distal end 238 is described as a contrast port 220, it is contemplated that the lumen 224 may be used for the passage of other devices (e.g., a guidewire) and/or therapeutic agents, as desired. An aperture 240 may be formed in a side wall of the outer tubular member 232 to define the second contrast port 222. It is contemplated that fluid exiting through the second contrast port 222 may flow away from, or at an angle to, the longitudinal axis L. While the aperture 240 is described as a contrast port 222, it is contemplated that the lumen 224 may be used for the passage of other devices (e.g., a guidewire) and/or therapeutic agents, as desired. In some cases, the contrast port 222 may be an open distal end of the outer tubular member 232 similar to the inner tubular member 230, as desired.

While a coaxial configuration is shown with inner and outer tubular members in FIGS. 4-5, a side-by-side configuration using a single extruded element with multiple lumens may be used instead. The illustrative example may use an over-the-wire configuration, in which a guidewire lumen is provided extending through the entire length of the balloon catheter, or a rapid exchange configuration in which the guidewire lumen is designed to cause the guidewire to exit relatively near the distal end of the balloon catheter, which allows a much shorter guidewire to be used. Coaxial and side-by-side configurations, as well as over-the-wire and rapid exchange configuration are well known in the balloon catheter technologies, and the present invention is not intended to be limited to any one such design.

Figure 6:
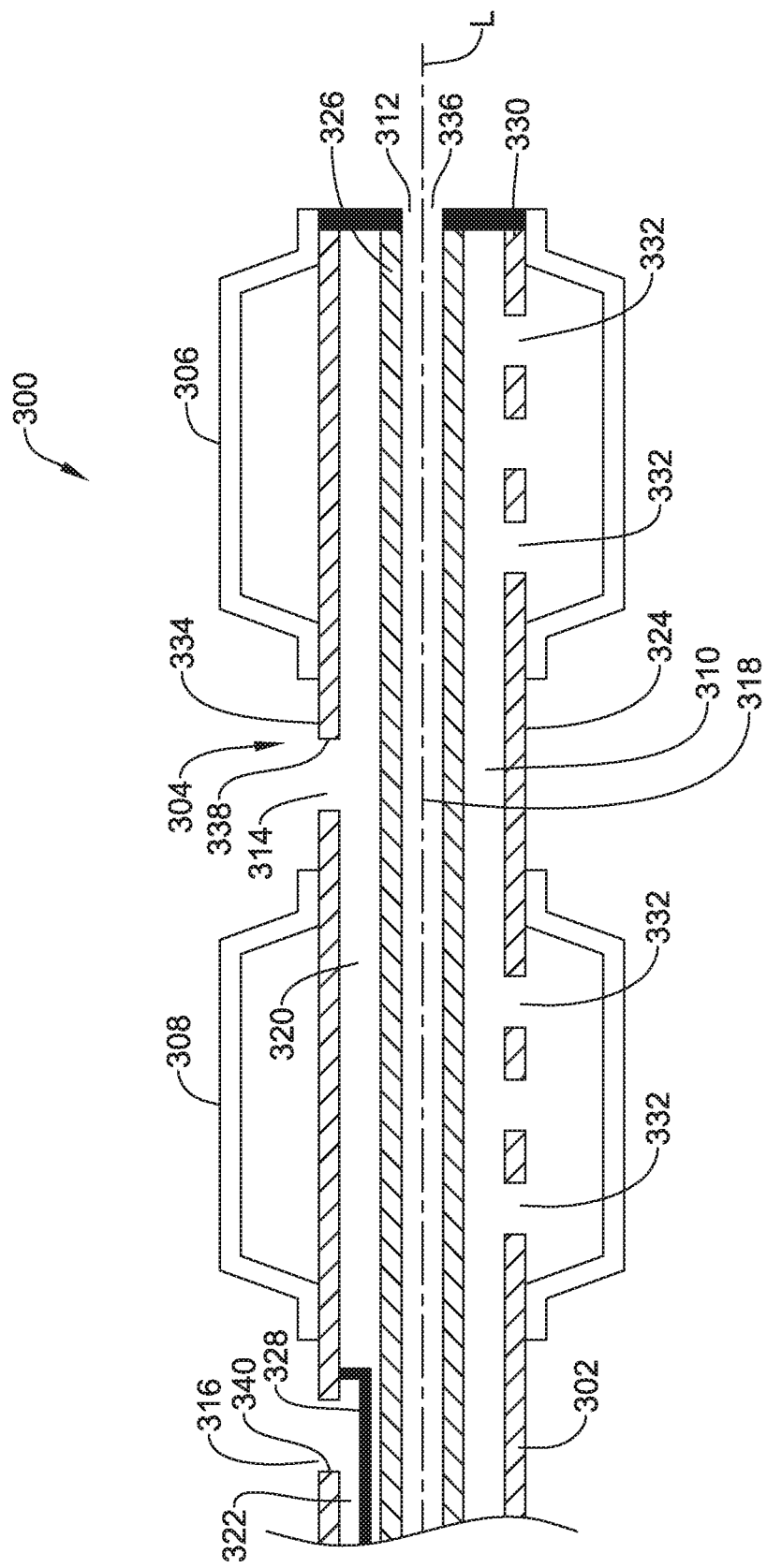
FIG. 6 shows a cross-sectional view of a distal portion of another illustrative illuminating catheter.

FIG. 6 illustrates a cross-sectional view of another illustrative balloon catheter 300, which may be used to selectively illuminate the ITV and/or vasculature connected thereto. The catheter 300 may be sized in length and diameter to reach the desired treatment region. For example, a 6 French catheter may be used to access the ITV while a 3 F catheter may be required to access the intercostal veins. The balloon catheter 300 may include an elongate shaft 302 extending from a proximal end region (not explicitly shown) to a distal end region 304. The catheter 300 may include a hub assembly (not explicitly shown) configured to remain outside of the body positioned adjacent to the proximal end of the elongate shaft 302. In some instances, the hub assembly may include one or more fluid injection ports, one or more accessory device ports and/or one or more Luer valve connections.

The catheter 300 may include a first or distal inflatable balloon 306 positioned adjacent to the distal end region 304 of the elongate shaft 302 and a second or proximal inflatable balloon 308 positioned proximal to the first inflatable balloon 306. The balloons 306, 308 may be in fluid communication with a first lumen or an inflation lumen 310 which may be in fluid communication with a Luer valve. While only a single inflation lumen 310 is illustrated, it is contemplated that the catheter 300 may include more than one inflation lumen such that the balloons 306, 308 may be inflated or expanded independently of one another. It is contemplated that the catheter 300 may be provided with more than two balloons. For example, three or more balloons may be positioned along a length of the catheter 300. In some cases, a contrast injection port may be provided between each balloon and at a distal end of the catheter 300 to allow contrast to be provided at any side vessel.

The balloons 306, 308 may be advanced through the vasculature in a collapsed or deflated state (not explicitly shown) and expanded or inflated once a target location has been reached. As will be described in more detail herein, the balloons 306, 308 may be inflated to block or otherwise direct the flow of a contrast agent. In some examples, a proximal portion of the first balloon 306 and/or a distal portion of the second balloon 308 may be generally planar and configured to extend generally perpendicular to the longitudinal axis L of the catheter 300. In some cases, one or both of the balloons 306, 308 may have a cone-like shape. If so provided, the tapers of the cone-like structure may be positioned away from one another such that the contrast may be distributed between the balloons 306, 308. A flat proximal surface of the first balloon 306 may redirect contrast flow in a direction proximal to the first balloon 306 while a flat distal surface of the second balloon 308 may direct contrast flow in a direction distal to the second balloon 308. It is contemplated that other balloon shapes may be used as desired to be control the flow of contrast, as desired.

The catheter 300 may further include a first contrast port or opening 312 positioned distal to the first balloon 306, a second contrast port or opening 314 positioned between the first balloon 306 and the second balloon 308, and a third contrast port or opening 316 positioned proximal to the second balloon 308. The first contrast port 312 is in fluid communication with a second lumen 318 which is in fluid communication with an injection port. The second contrast port 314 is in fluid communication with a third lumen 320 which is in fluid communication another injection port. The third contrast port 316 is in fluid communication with a fourth lumen 322 which is in fluid communication another injection port. In some embodiments, the second and third contrast ports 314, 316 may be in fluid communication with a shared lumen.

The first lumen 310, the second lumen 318, the third lumen 320, and the fourth lumen 322 may extend within or otherwise be a part of the elongate shaft 302. In some embodiments, the elongate shaft 302 may be an extruded multi-lumen shaft 302. In other embodiments, the elongate shaft 302 may be formed from a plurality of individual tubes, each defining a lumen, which have been laminated, or otherwise bonded, together.

In the illustrated embodiment, the elongate shaft 302 includes a first tubular member 324, a second tubular member 326, a third tubular member 334, and a fourth tubular member 328. The first and third tubular members 324, 334 extend from the proximal region to the distal end 330 of the catheter 300. The balloons 306, 308 may be affixed to an outer surface of the first and third tubular members 324, 334. In some cases, the first tubular member 324 and the fourth tubular member 334 may be formed from single tubular member including a partitioning wall to define two or more lumens. In some instances, the first tubular member 324 may include one or more apertures 332 extending from the inflation lumen 310 to the interior of the inflation balloons 306, 308. Apertures 332 may allow inflation fluid to enter the balloons 306, 308. The third tubular member 334 defines the third lumen 320 that extends through the elongate shaft 302.

The second tubular member 326 extends from the proximal region of the elongate shaft 302 and through the distal end region 304 of the elongate shaft 302 to the distal end 330 of the catheter 300. The second tubular member 326 defines the second lumen 318 that extends through the elongate shaft 302. The fourth tubular member 328 extends from the proximal region of the elongate shaft 302 to a point proximal to the second balloon 308. In some cases, the fourth tubular member 328 may extend to the distal end 330 of the catheter 300. In such a case, the fourth tubular member 328 may include a wall or other barrier mechanism to direct fluid out of the third contrast port 316. The fourth tubular member 328 defines the fourth lumen 322 that extends through the elongate shaft 302. In some cases, the fourth tubular member 328 may be formed by including a barrier wall within the third tubular member 334, as shown in FIG. 6, although this is not required.

The second tubular member 326 may terminate in an open distal end 336 defining the first contrast port 312. It is contemplated that fluid exiting through the first contrast port 312 will generally flow in line with a longitudinal axis of the catheter 300. While the open distal end 336 is described as a contrast port 312, it is contemplated that the lumen 318 may be used for the passage of other devices (e.g., a guidewire) and/or therapeutic agents, as desired. A first aperture 338 may be formed in a side wall of the third tubular member 334 to define the second contrast port 314. A second aperture 340 may be formed in a side wall of the third tubular member 334 to define the third contrast port 316. It is contemplated that fluid exiting through the second and third contrast ports 314, 316 may flow away from, or at a non-parallel angle to, the longitudinal axis L. While the apertures 228, 240 are described as contrast ports 314, 316, it is contemplated that the lumens 320, 322 may be used for the passage of other devices (e.g., a guidewire) and/or therapeutic agents, as desired. In some cases, one or both of the second and third contrast ports 314, 316 may be configured such that fluid exits the ports 314, 316 in a flow direction parallel to the longitudinal axis L.

Figure 7:
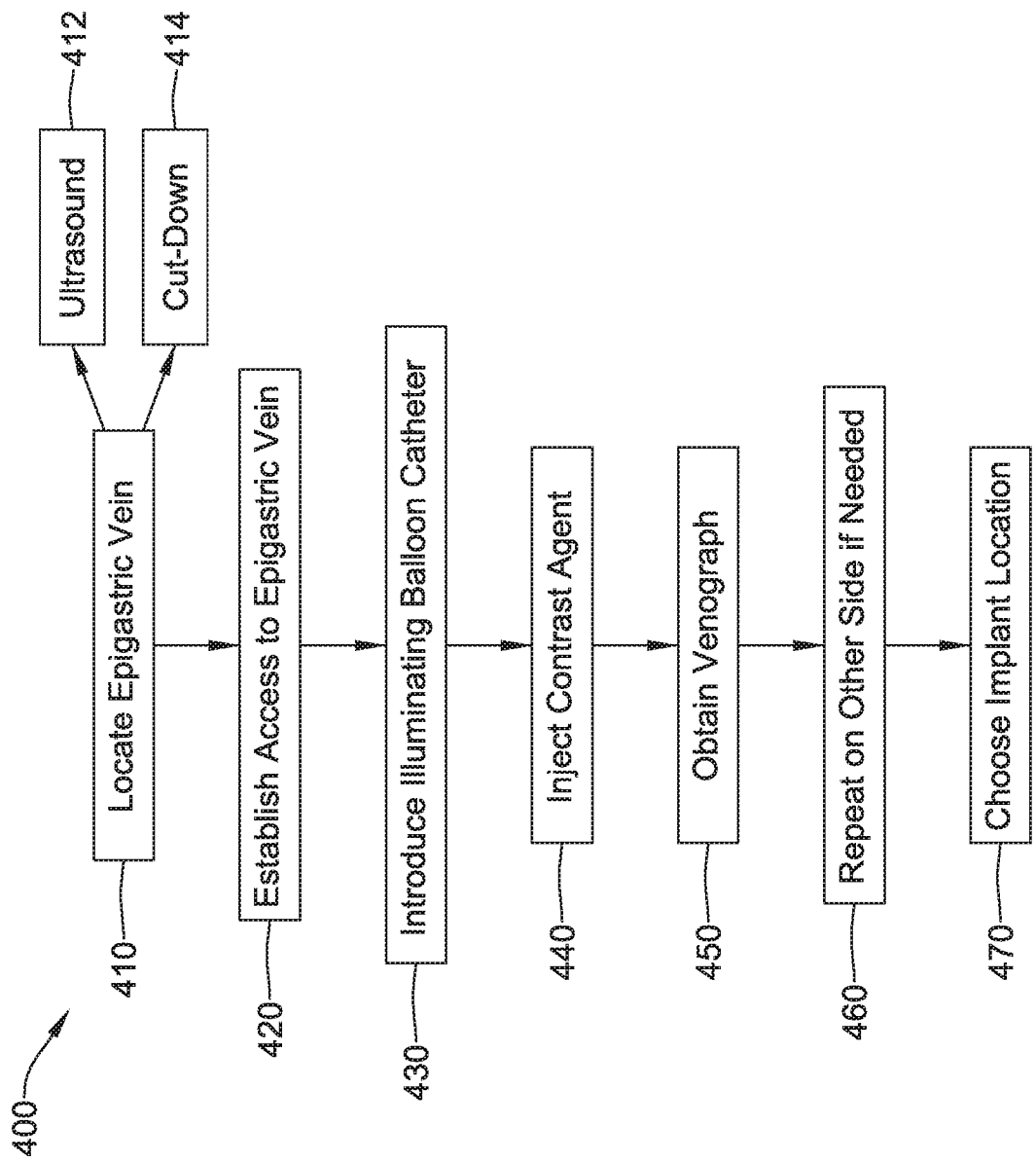
FIG. 7 is a block flow diagram for an illustrative method.

FIG. 7 is a block flow diagram for an illustrative method 400 for identifying an appropriate vein for implanting a cardiac stimulus system to a patient. As shown at 400, the method may generally comprise locating a left or right musculophrenic or superior epigastric vein 410, establishing access to the left or right musculophrenic or superior epigastric vein 420, introducing an illuminating balloon catheter to the musculophrenic or superior epigastric vein 430, injecting a contrast agent into the vein 440, and obtaining a venograph 450. Any contrast agent suitable for use in the bloodstream may be used; various are known in the art. In some cases, the method steps of locating a left or right musculophrenic or superior epigastric vein 410, establishing access to the left or right musculophrenic or superior epigastric vein 420, introducing an illuminating balloon catheter to the musculophrenic or superior epigastric vein 430, injecting a contrast agent into the vein 440, and obtaining a venograph 450 may be repeated 460 on the opposite side, if necessary.

The implant location may be chosen 470 based on the venograph(s) obtained in step 450. For example, the venography may reveal whether the intercostal blood vessels are large enough, or too small, to receive an implantable lead having dimensions of in the range of 1-3 French. If the venography reveals that the intercostal veins are of sufficient size, then a lead may pass into or through the intercostal veins, for example, to reach a lateral axillary position where the lead exits to a subcutaneous position for an implantable pulse generator canister, such as in U.S. patent application Ser. No. 15/846,081, titled IMPLANTATION OF AN ACTIVE MEDICAL DEVICE USING THE INTERCOSTAL VEIN, or for attachment to a patch electrode as in U.S. Provisional Patent Application No. 62/486,635, titled ACTIVE MEDICAL DEVICE WITH ATTACHMENT FEATURES, the disclosures of which are incorporated herein by reference. In another example, the intercostal vein may be accessed as the end point for a lead that extends downward from the subclavicular region, with the lead entering the subclavian vein, then to the brachiocephalic vein, then into an ITV and finally into an intercostal vein, as in U.S. patent application Ser. No. 15/868,799, titled IMPLANTATION OF AN ACTIVE MEDICAL DEVICE USING THE INTERNAL THORACIC VASCULATURE, the disclosure of which is incorporated herein by reference. In still another example, the lead may wrap around to the back of the patient, either from an ITV or beginning at an axillary position using an intercostal vein, as in U.S. patent application Ser. No. 15/847,490, titled AZYGOS, INTERNAL THORACIC, AND/OR INTERCOSTAL VEIN IMPLANTATION AND USE OF MEDICAL DEVICES, the disclosure of which is incorporated herein by reference.

On the other hand, if the intercostal veins are not of sufficient size, then a lead may exit the ITV, the musculophrenic vein, or the superior epigastric vein, and be advanced subcutaneously to a desired end position for a lead electrode or canister placement, as in US PG Patent Pub. No. 20180036527, and/or U.S. patent application Ser. No. 15/801,719, titled PARASTERNAL PLACEMENT OF AN ACTIVE MEDICAL DEVICE USING THE INTERNAL THORACIC VASCULATURE, the disclosures of which are incorporated herein by reference. In another example, the sizing determined from the venograph may be used to determine whether the ITV itself can be used, or whether the left or right ITV should be used. Positioning of the blood vessels may also be determined using the venograph by, for example, observing whether either ITV or an intercostal vein is located adjacent a desired cardiac structure such as the right or left atria, which may be a useful position for a sensing lead or electrode, or right or left ventricles, which may be useful for therapy delivery and/or sensing electrodes, or for placement of specific sensors (acoustic/vibrational or motion, for example). In still another example, positioning may be useful to select a desirable position for placement of a transducer to generate an output energy, such as an ultrasonic transducer that may be placed in the ITV or in an intercostal vein to stimulate a leadless cardiac pacemaker in the heart, as discussed in U.S. patent application Ser. No. 15/847,435, titled INTERNAL THORACIC VEIN PLACEMENT OF A TRANSMITTER ELECTRODE FOR LEADLESS STIMULATION OF THE HEART, the disclosure of which is incorporated herein by reference.

For example, locating a left or right musculophrenic or superior epigastric vein 410 may include locating the vein at or near the sub-xiphoid region using ultrasound guidance 412. In some cases, ultrasound guidance may be used in combination with a Valsalva maneuver, although this is not required. In other embodiments, a cut-down technique 414 may be used to locate the musculophrenic or superior epigastric vein. In some examples, because the musculophrenic vein is known to run alongside the most inferior rib bone, that vein may be identified more readily.

Figure 8:
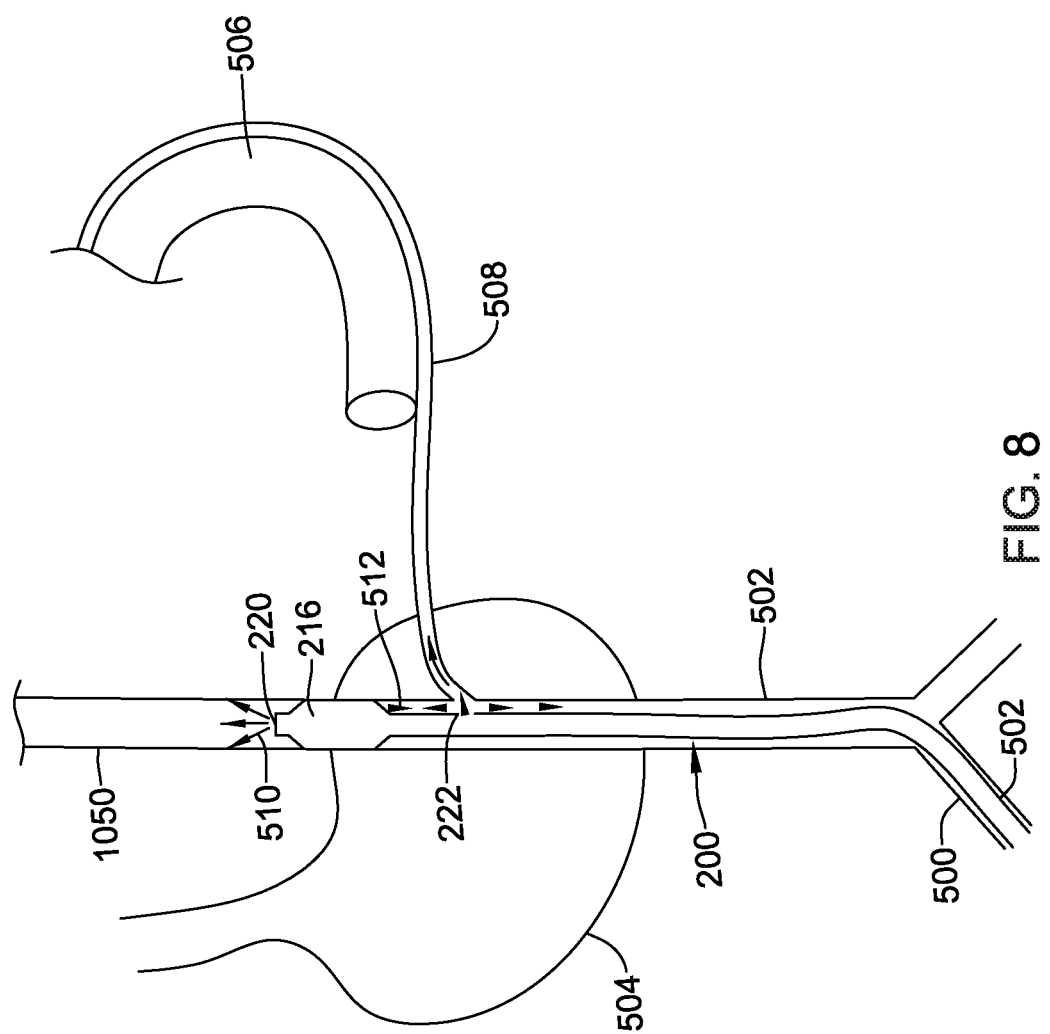
FIG. 8 shows an illuminating catheter in an ITV.

In an example, establishing access to the musculophrenic or superior epigastric vein 420 may include accessing the vein using a Seldinger technique. Once the musculophrenic or superior epigastric vein has been accessed, an illuminating balloon catheter, such as the balloon catheters 200, 300 described herein, are introduced into the vein 430. FIG. 8 is an anterior view of a portion of an illustrative method for introducing an illuminating balloon catheter 200 into the musculophrenic or superior epigastric vein 500. While the Figure is described with reference to catheter 200, it should understood that any suitable illuminating catheter such as, but not limited to catheter 200 may be used. Referring now to FIG. 8, in this example, a patient is shown in an anterior lateral view with relevant elements shown in isolation for clarity purposes. The superior epigastric vein is shown at 500 (item 500 may be the left or right superior epigastric vein), and the ITV is shown at 502 (item 502 may be the left or right ITV), passing generally over the heart 504 and beneath the ribs 506. An intercostal vein 508 is shown adjacent to the rib 506 and draining to the ITV 502. For clarity, only a single rib 506 is illustrated and portions have been removed to better illustrate the ITV 502 and other anatomical features. The method may also be performed using the musculophrenic vein as the point of insertion.

The illuminating catheter 200 may be advanced until the balloon 216 is adjacent to a target implant region. While the catheter 200 is illustrated as being advanced from an inferior location, it is contemplated that the ITV 500 may be accessed from a superior location, an intercostal location, or using a cut-down technique, as desired. In some cases the catheter 200 may be advanced over a guidewire, while in other cases, the catheter 200 may be advanced without the use of a guidewire. The catheter 200 may include one or more radiopaque markers positioned along a length thereof to guide the placement of the balloon 216 using fluoroscopy. Once the catheter 200 has been positioned, the balloon 216 may be inflated, for example by injecting a suitable inflation fluid (e.g., air, saline, etc.) through the Luer valve 214. When so provided, the balloons on a catheter including more than one balloon may be selectively inflated to selectively visualize the vasculature. For example, a distal balloon may be inflated to allow for visualization of the vasculature proximal to the balloon. The catheter may then be repositioned and/or a second balloon inflated to allow for visualization of another part of the vasculature (e.g., the side branches). This is just one example and is not intended to be limiting. The catheters 200, 300 may be manipulated in any number of different ways to provide contrast agent to a desired location.

Referring additionally to FIG. 7, a contrast agent may be injected into the catheter 440. The contrast agent may be injected to each contrast port 220, 222 simultaneously or individually, as desired to cause a flow of contrast agent 510 exiting the distal port 220 and/or a flow of contrast agent 512 exiting the proximal port 222. The contrast agent 510, 512 may naturally flow towards the bigger braches in the nearby system due to the lower pressure in the larger branches. It is contemplated that since separate injection ports 210, 212 and lumens 224, 226 are provided, the contrast exit port 220, 222 may be selected on the need. For example, the more distal port 220 may be selected to more particularly illuminate the vein system superior to the device 200. The more proximal port 222 may be selected to more particularly illuminate the vein system inferior to and/or lateral to the device 200. The balloon 216 may prevent the contrast agent from migrating away from its intended direction. It is further contemplated that the catheter may also be selected based on need. For example, the dual balloon catheter 300 described with respect to FIG. 6 may be used to more particularly isolate portions of the anatomy.

Referring again to FIG. 7, once the contrast agent has been injected 440 a venograph is taken 450. In some cases, multiple venographs may be taken 450 to obtain a full understanding of the musculophrenic and/or epigastric vein, the ITV, and the peripheral veins thereof. It is contemplated that prior to each venography being taken, the catheter (e.g., catheter 200 or catheter 300) may be repositioned to better direct the contrast agent. The balloon 216 or balloons 306, 308 may be deflated and reinflated to accommodate repositioning, as needed.

In some cases, the method steps of locating a left or right musculophrenic vein or superior epigastric vein 410, establishing access to the left or right musculophrenic vein or left or right superior epigastric vein 420, introducing an illuminating balloon catheter to the musculophrenic vein, the superior epigastric vein 430, injecting a contrast agent into the vein 440, and obtaining a venograph 450 may be repeated 460 on the opposite side, if necessary. The implant location may be chosen 470 based on the venograph(s) obtained in step 450. It is contemplated that the implant location may be selected based on the size of the vein and the relative placement of the lead relative to the heart.

In another alternative example, block 410 may be substituted by indicating instead that access is made to the subclavian vein using standard subclavian access techniques, such as a cut-down or one of several variants on the Seldinger technique. For example, referring to FIG. 1A, the visualization catheter, with or without the aid of a sheath or guidewire, may be advanced from the subclavian vein 16 into the brachiocephalic vein 14 and, if crossing from right to left or left to right, through a portion of the SVC 12. The visualization catheter can then be advanced, with or without guidewire assistance in an inferior direction into the ITV 20. Use of a guidewire may be helpful during advancement in an inferior direction into the ITV 20 as the direction of movement will be counter to blood flow controlling valves in the ITV 20. The visualization catheter can then be used to inject contrast lumen in a controlled space to aid in sizing and visualizing the ITV 20 and intercostal veins 38. In still a further example, the visualization catheter may also or instead be advanced into the azygos vein 18, allowing again visualization of the azygos vein 18 itself or, if accessing the posterior left side of the patient's chest, the hemiazygos or accessory hemiazygos veins and/or the intercostal veins in the region thereof.

Figure 9:
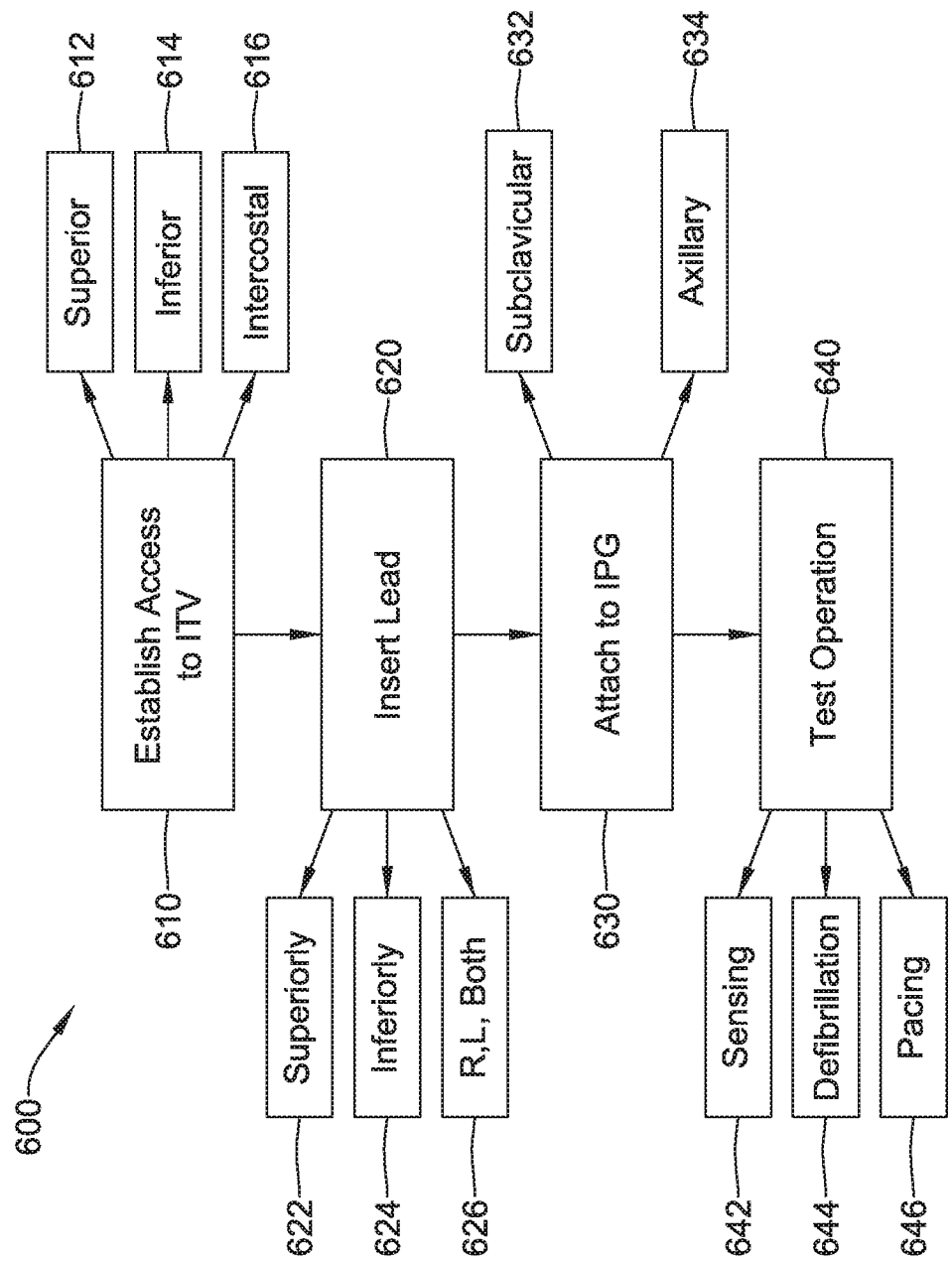
FIG. 9 is a block flow diagram for an illustrative method.

FIG. 9 is a block flow diagram for an illustrative method for providing a cardiac stimulus system to a patient. As shown at 600, the method comprises establishing access to the ITV 610, inserting a lead in the ITV 620, attaching an IPG to the lead 630, and performing test operations 640.

For example, establishing access to the ITV 610 may include accessing from a superior position 612 such as by entering the subclavian vein and passing through the ostium of the ITV in the brachiocephalic vein. In another example, establishing access to the ITV 610 may include accessing from an inferior position 614 such as by entering the superior epigastric vein or musculophrenic vein and passing superiorly therefrom into the ITV. In some examples, access via locations 612, and 614 may include accessing via a second blood vessel such as by accessing superiorly 612 by way of the subclavicular vein and brachiocephalic vein, or accessing inferiorly 614 through the superior epigastric vein or musculophrenic vein. In still another example, establishing access to the ITV may include accessing in an intercostal space 616 such as by penetrating an intercostal space and entering the ITV using a Seldinger technique.

In an example, inserting a lead 620 may include insertion superiorly 622, such as by starting in an inferior position 612 inferior to the lower rib margin or intercostally 616 from an inferior intercostal location, and advancing the lead in a superior direction. For another example, inserting a lead 620 may include insertion inferiorly 624 that is, starting at a superior location 614 or at a superior intercostal location 616, and advancing the lead in an inferior direction. In either such example, the right ITV, left ITV, or both ITV vessels may be used, as indicated at 626.

Other vessels and implanted lead locations may also be used (such as having a lead in the azygos vein, an intracardiac lead, and/or a subcutaneous lead) or additional devices such as a separately implanted leadless cardiac pacemaker may be included as well. In a further example, one or more of the transverse veins that flow into the ITV may be used for placement of an electrode or lead. For example, upon accessing an ITV, a physician may further access and emplace a lead or electrode into one of the anterior intercostal veins which run along the intercostal spaces of the anterior chest.

In an example, attaching to an IPG may include attaching to a canister located in a subclavicular location 632, historically a common place to put an implanted canister for a transvenous defibrillator or pacemaker. In another example, attaching to an IPG may include attaching to a canister located in an axillary position 634, such as that used with the S-ICD System. Other IPG locations may be used. Attachment may be directly to the IPG or to a splitter, yoke, or lead extension, if desired.

In an example, test operation 640 may be used to verify one or both of device functionality and efficacy. For example, sensing operations 642 may be tested and configured to check for adequate signal availability, for example, or by setting gain, filtering, or sensing vector selection parameters. Defibrillation operations 644 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 644 may include determining for a given patient an appropriate defibrillation threshold, and setting a parameter for therapy delivery at some safety margin above the defibrillation threshold.

Prior transvenous systems would typically deliver up to 35 Joules of energy at most, with storage of up to 40 Joules of energy, using peak voltages in the range of up to nearly 1000 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation 646 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

In some cases, the left and/or right ITV may be used to access an intercostal vein. Electrodes may be placed in the intercostal veins in addition to or in place of electrodes in the ITV to increase the number of lateral and posterior defibrillation vectors which may further reduce defibrillation thresholds. From such a position, beneath the rib cage, the amount of energy required for defibrillation and pacing efficacy would logically be lower than outside of the sternum and/or rib cage, since the ITV location is closer to the heart and bone is generally not a very good conductor of electrical energy, at least when speaking in terms of the tissues in the human body.

Figure 10:
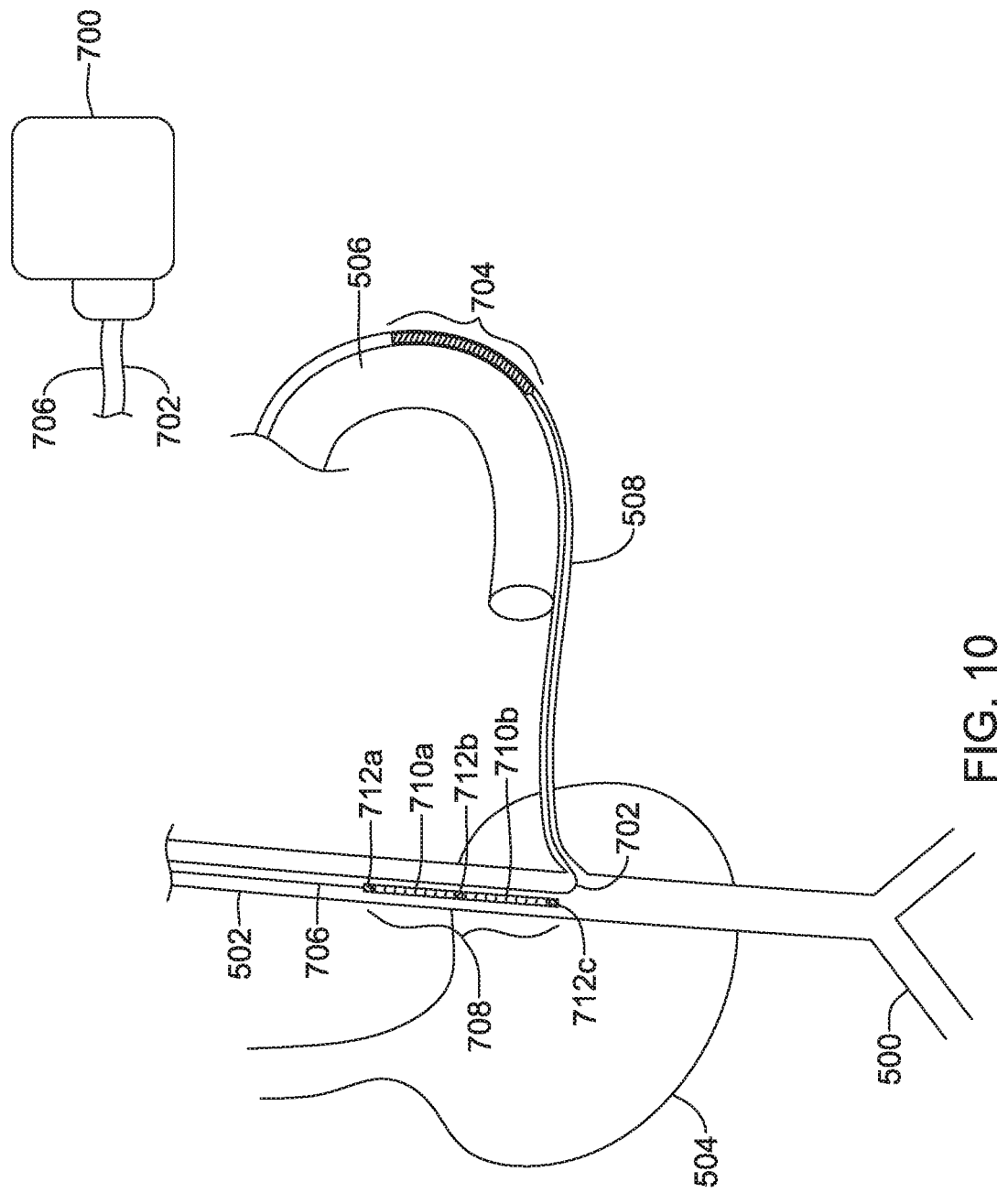
FIG. 10 shows an illustrative lead in an ITV and an illustrative lead in an intercostal vein.

FIG. 10 shows an implantable cardiac stimulus device in the intercostal vein 508 and the ITV 502. The system includes an implantable pulse generator 700 which may be placed in a subclavicular location, at the anterior axillary line, the midaxillary line, or in the posterior axillary line (or any other suitable position, as desired). The pulse generator 700 may be placed as shown in US PG Patent Pub. No. 20180036547, titled PACEMAKERS FOR IMPLANT IN THE INTERNAL THORACIC VASCULATURE WITH COMMUNICATION TO OTHER IMPLANTABLE DEVICES, the disclosure of which is incorporated herein by reference.

A lead 702 passes into the intercostal vein 508 through the ITV 502. The lead 702 may be passed laterally and posteriorly through the intercostal vein 508. In some cases, the lead 702 may extend through the anterior intercostal vein and into the posterior intercostal vein. Positioning the lead 702 in a more lateral and/or more posterior position relative to the heart 504 may further reduce the defibrillation thresholds relative to a lead 702 positioned closer (laterally and/or anteriorly) to the heart.

In the example, the lead 702 includes a coil electrode as shown at 704. The coil electrode 704 may be a high voltage coil that may also serve as a pacing anode. However, any lead design may be used, as desired. Further, while an anchoring mechanism is not explicitly shown, the lead can be fixated in the vasculature using various means such as tines, hooks, biases, T-bar tethers, and other means. In addition to the engaging members described herein some illustrative additional anchoring mechanisms are discussed in US PG Patent Publication 20170021159, titled SUBSTERNAL PLACEMENT OF A PACING AND/OR DEFIBRILLATING ELECTRODE, as well as US PG Patent Publication 20170095657, titled FIXATION DEVICE FOR A SUBCUTANEOUS ELECTRODE, the disclosures of which are incorporated herein by reference. The proximal end of the lead 702 may be connected to an implantable pulse generator 700.

In some cases, the lead 702 may be placed on the left side of the patient. In other examples, the right side of the patient may instead or in addition be accessed, including the right ITV. Access to the right ITV may be achieved by advancing a guide catheter and/or guidewire from in any of the manners described herein.

In some examples, a lead 702 may be placed in intercostal veins from the left and right ITVs. In such an instance, a lead 702 is delivered through each of the left and right ITV to an intercostal vein. Pacing between right and left side lead placements may be performed to target specific chambers or chamber combinations, or sensing may be performed using one pair of electrodes with therapy delivery using a different pair of electrodes to achieve resynchronization or other desirable effect.

In the example, a second lead 706 includes a multi-electrode distal structure as shown at 708. However, any lead design may be used, as desired. Further, while an anchoring mechanism is not explicitly shown, the lead can be fixated in the mediastinum using various means such as tines, hooks, biases, T-bar tethers, and other means. In addition to the engaging members described herein some illustrative additional anchoring mechanisms are discussed in US PG Patent Publication 20170021159, titled SUB- STERNAL PLACEMENT OF A PACING AND/OR DEFIBRILLATING ELECTRODE, as well as US PG Patent Publication 20170095657, titled FIXATION DEVICE FOR A SUBCUTANEOUS ELECTRODE, the disclosures of which are incorporated herein by reference. In some cases, the leads 702, 706 may be combined into or connected to a single wire for connection to the pulse generator 700, although this is not required.

In some cases, the lead 706 may be placed on the left side of the patient. In other examples, the right side of the patient may instead or in addition to be accessed, including the right ITV. Access to the right ITV may be achieved by advancing a guide catheter and/or guidewire from in any of the manners described herein.

In some examples, a lead 706 may be placed in both the left and right ITVs. In such an instance, a lead 706 is delivered through each of the left and right ITV. Pacing between right and left side lead placements may be performed to target specific chambers or chamber combinations, or sensing may be performed using one pair of electrodes with therapy delivery using a different pair of electrodes to achieve resynchronization or other desirable effect.

In this example, the lead structure includes a proximal coil 710A separate from a distal coil 710B. The coils 710A/B and canister 700 may serve as therapy delivery electrodes. As such there may be multiple therapy vectors such as between coil 710A and coil 710B, between either of coils 710A and 710B and the canister 700, or between a combination of two of the three therapy electrodes 710A, 710B and canister 700, and the third such electrode, such as by linking coils 710A and 710B in common as the anode or cathode relative to the canister 700. Alternatively, or additionally vectors may be between either of coils 710A and 710B and the coil electrode 704 in the intercostal vein 508.

A plurality of ring electrodes may be provided as shown at 712A, 712B, and 712C. Electrode 712C may also or instead be a tip electrode. Electrodes 712A/B/C may serve as sensing electrodes. The coils 710A, 710B may also serve as sensing electrodes. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, US PG Publication No. 20170113053, titled SIGNAL QUALITY MONITORING FOR MULTIPLE SENSE VECTORS IN CARDIAC DEVICES, US PG Publication No. 20170113050, titled MULTI-VECTOR SENSING IN CARDIAC DEVICES WITH DETECTION COMBINATIONS, US PG Publication No. 20170113040, titled MULTI-VECTOR SENSING IN CARDIAC DEVICES WITH SIGNAL COMBINATIONS, and/or US PG Publication No. 20170112399, titled MULTI-VECTOR SENSING IN CARDIAC DEVICES USING A HYBRID APPROACH.

In addition, one or more of the ring or tip electrodes 712A, 712B, 712C may be used for therapy delivery. In an example, defibrillation therapy may use coils 710A, 710B coupled in common as the opposing pole to the canister 700, while pacing therapy may use coils 710A and 712B as opposing electrodes for post-shock pacing therapy, with a still different combination of electrodes used to provide ventricular pacing therapy for example by pacing between coil 710B and tip electrode 712C. In some embodiments, the coil electrode 704 positioned in the intercostal vein 508 may also be used as an opposing electrode for post-shock packing therapy or ventricular pacing therapy.

The lead 700 may be placed as shown such that the proximal coil 710A is about level with the atria, and distal coil 710B is about level with the ventricles, if desired. In some examples fewer or different electrodes may be provided on the lead 700 such as by excluding one or the other of the proximal coil 710A or distal coil 710B. In some examples, one or more electrodes on the lead 700 are provided at or inferior to the apex of the heart 504, or at or superior to the top of the heart 504.

As described above, placing electrodes in the ITV 502 as well as an intercostal vein 508 provides lateral and posterior defibrillation vectors which may reduce defibrillation thresholds. Accessing the intercostal vein 508 through the brachiocephalic vein may allow for the placement of a combination internal thoracic vein lead and an intercostal vein lead (offering an anterior to lateral/posterior defibrillation vector) through a single access point and a left pectoral canister 700 placement (although other canister locations can be used). It is further contemplated that the ITV 502 and/or the intercostal vein 508 may be accessed through the musculophrenic vein, the superior epigastric vein or intercostally. Further, it is contemplated a lead may be placed in one of the ITV 502 or the intercostal vein 508 without placement of a lead in the other.

Figure 11:
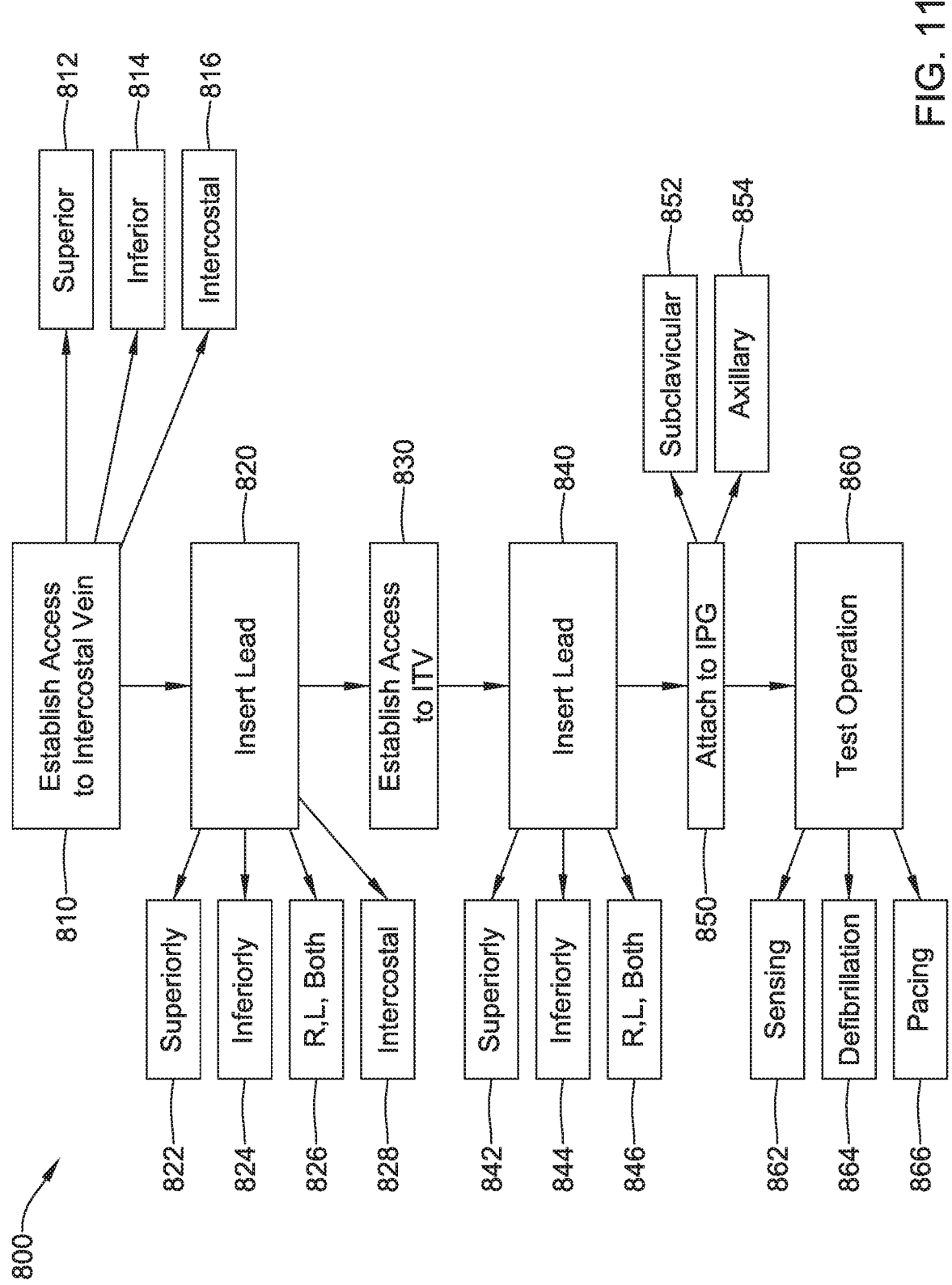
FIG. 11 is a block flow diagram for an illustrative method.

FIG. 11 is a block flow diagram for an illustrative method for providing a cardiac stimulus system to a patient. As shown at 800, the method comprises establishing access to the intercostal vein 810, inserting a lead in the intercostal vein 820, establishing access to the ITV 830, inserting a lead in the ITV 840, attaching an IPG to the lead(s) 850, and performing test operations 860.

For example, establishing access to the intercostal vein 810 may include accessing from a superior position 812 such as by entering the subclavian vein and passing through the ostium of the ITV in the brachiocephalic vein and then entering the intercostal vein from the ITV. In another example, establishing access to the intercostal vein 810 may include accessing from an inferior position 814 such as by entering the superior epigastric vein or musculophrenic vein and passing superiorly therefrom into the ITV and then entering the intercostal vein from the ITV. In some examples, access via locations 812, and 814 may include accessing via a second blood vessel such as by accessing superiorly 812 by way of the subclavicular vein and brachiocephalic vein, or accessing inferiorly 814 through the superior epigastric vein or musculophrenic vein. In still another example, establishing access to the intercostal vein 810 may include accessing in an intercostal space 816 such as by penetrating an intercostal space and entering the ITV using a Seldinger technique.

In an example, inserting a lead 820 into the intercostal vein may include insertion superiorly 832, such as by starting in an inferior position 812 inferior to the lower rib margin and advancing the lead in a superior direction. For another example, inserting a lead 820 may include insertion inferiorly 824 that is, starting at a superior location 814 or at a superior intercostal location 816, and advancing the lead in an inferior direction. In either such example, the right ITV, left ITV, or both ITV vessels may be used to place a lead in the intercostal vein, as indicated at 836. Alternatively, the intercostal vein may accessed directly 828 via the intercostal space 816.

Establishing access to the ITV 830 may include accessing from a superior position 812 such as by entering the subclavian vein and passing through the ostium of the ITV in the brachiocephalic vein. In another example, establishing access to the ITV 830 may include accessing from an inferior position 814 such as by entering the superior to epigastric vein or musculophrenic vein and passing superiorly therefrom into the ITV. In some examples, access via locations 812, and 814 may include accessing via a second blood vessel such as by accessing superiorly 812 by way of the subclavicular vein and brachiocephalic vein, or accessing inferiorly 814 through the superior epigastric vein or musculophrenic vein. In still another example, establishing access to the intercostal vein 810 may include accessing in an intercostal space 816 such as by penetrating an intercostal space and entering the ITV using a Seldinger technique.

In an example, inserting a lead in the ITV 840 may include insertion superiorly 842, such as by starting in an inferior position 812 inferior to the lower rib margin or intercostally 816 from an inferior intercostal location (e.g., via an intercostal vein), and advancing the lead in a superior direction. For another example, inserting a lead 840 may include insertion inferiorly 844, that is starting at a superior location 814 or at a superior intercostal location 816 (e.g., via an intercostal vein), and advancing the lead in an inferior direction. In either such example, the right ITV, left ITV, or both ITV vessels may be used to place a lead in the mediastinum, as indicated at 846.

During the implantation procedures, contrast or other visualization may be used in various ways. For example, when using a superior access 812 to the ITV, entering for example via the brachiocephalic vein, contrast or other visualization may be used to track the position of a guidewire, guide catheter or the lead itself into the ostium and then down in to the ITV. In addition, regardless the access route to the ITV, the step of establishing access to the mediastinum may include use of visualization to observe the exit from the ITV and into the mediastinum. Lateral X-ray or other visualization may be used as well to observe lead positioning both in terms of how superior/inferior the lead and its electrodes are, as well as whether the lead is deep enough or shallow enough, as the case may be, in the mediastinum to achieve therapy and/or anchoring aims, and to avoid piercing or poking the lung and/or pericardium, if desired.

Other vessels and implanted lead locations may also be used (such as having a lead in the right ITV, left ITV, both ITVs, azygos vein, an intracardiac lead, a subcutaneous lead) or additional devices such as a separately implanted leadless cardiac pacemaker may be included as well. In a further example, one or more of the transverse veins that flow into the ITV may be used for placement of an electrode or lead. For example, upon accessing an ITV, a physician may further access and emplace a lead or electrode into one of the anterior intercostal veins which run along the intercostal spaces of the anterior chest.

In an example, attaching to an IPG may include attaching to a canister 850 located in a subclavicular location 852, historically a common place to put an implanted canister for a transvenous defibrillator or pacemaker. In another example, attaching to an IPG may include attaching to a canister located in an axillary position 854, such as that used with the S-ICD System. Other IPG locations may be used. Attachment may be directly to the IPG or to a splitter, yoke, or lead extension, if desired.

In an example, test operation 860 may be used to verify one or both of device functionality and efficacy. For example, sensing operations 862 may be tested and configured to check for adequate signal availability, for example, or by setting gain, filtering, or sensing vector selection parameters. Defibrillation operations 864 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 864 may include determining for a given patient an appropriate defibrillation threshold, and setting a parameter for therapy delivery at some safety margin above the defibrillation threshold.

Prior transvenous systems would typically deliver up to 35 Joules of energy at most, with storage of up to 40 Joules of energy, using peak voltages in the range of up to nearly 1300 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation 866 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

In some cases, the left and/or right ITV may be used to access the mediastinum. The target location in region generally contains some loose connective tissues, muscle, nerves and blood vessels. Anchoring a lead may be desirable, for example, in the region between the left and/or right ITV (and beneath the rib cage) and a lateral side of the heart. From such a position, beneath the rib cage, the amount of energy required for defibrillation and pacing efficacy would logically be lower than outside of the sternum and/or rib cage, since the mediastinum location is closer to the heart and bone is generally not a very good conductor of electrical energy, at least when speaking in terms of the tissues in the human body. However, tunneling in this region is not as necessary as it may be in other locations, particularly the subcutaneous space, where the innermost layers of dermis must be separated from underlying muscle, connective tissue and fascia. Indeed, the insertion of a lead through the ITV (e.g., using any of superior access, inferior access, and/or intercostal access) may enable safe placement in the mediastinum.

In any of the above examples, additional lead placement may take place. For example, an additional lead may be placed subcutaneously, within the heart, or in a different blood vessel such as the azygos vein. Additional device placement may occur as well, including, for example, the placement of a leadless cardiac pacemaker in one or more chambers of the heart.

The above examples facilitate a number of therapy options. For example, defibrillation therapy may be delivered in various configurations such as, without limitation:
Between a left ITV electrode or combination of electrodes and a right ITV electrode or combination of electrodes;

Between a left ITV electrode and a device housing placed in the left axilla or left subclavicular location;

Between a right ITV electrode and a device housing placed in the left axilla or left subclavicular location;

Between a left ITV electrode and a device housing placed in the right axilla or right subclavicular location;

Between left and right ITV electrodes electrically in common and a right or left axillary or subclavicular canister;

Between one ITV electrode and a second ITV electrode in common with a device canister in the left or right axilla or subclavicular location;

Between a first electrode on a lead, and a second electrode on the same lead, where the first and second electrodes are in the same ITV;

Between a first electrode on a lead, and a second electrode on the same lead, where the first electrode is in an ITV, and the second electrode is in a tunnel leading to access to the ITV, such as in the inframammary crease;

Between a left ITV electrode or combination of electrodes and a left axilla electrode or combination of electrodes;

Between a right ITV electrode or combination of electrodes and a right axilla electrode or combination of electrodes;

Between a left ITV electrode or combination of electrodes and a right axilla electrode or combination of electrodes;

Between a right ITV electrode or combination of electrodes and a left axilla electrode or combination of electrodes.

In these examples, a "left ITV electrode" or "right ITV electrode" may include a single coil electrode or a combination of plural coils and/or one or more coils with one or more ring electrodes electrically in common. The above combinations may also be used for delivery of a bradycardia pacing therapy or an anti-tachyarrhythmia pacing therapy.

Further examples may provide a resynchronization therapy by delivering pacing pulses in various configurations, such as, without limitation:

In bipolar fashion within the left ITV to pace the left ventricle, and also in bipolar fashion within the right ITV to pace the right ventricle, with relative timing between the two sets of pacing therapies determined according to analysis of cardiac output or electrical response.

In bipolar fashion within one of the left or right ITV to stimulate a respective left or right ventricle in response to atrial sensed signals sensed with electrodes placed in an ITV at a superior location level with the atria.

In monopolar fashion between a device housing and one or both of left or right ITV electrodes, using for timing information atrial signals sensed using additional electrodes in at least one ITV and/or far-field sensed morphology detected using a device housing.

In an example, a heart failure or resynchronization therapy may be delivered as follows. A pacing therapy may be delivered by sensing atrial activity using two distal ring electrodes in an electrode assembly to determine timing for pace therapy delivery using the proximal coil electrode and canister. Numerous other combinations may be had as can be seen to those skilled in the art.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

Each of these non-limiting examples can stand on its own, or can be combined in to various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method for identifying an implant location for implanting a lead for use in a cardiac stimulus system in a patient, the lead having at least one electrode thereon; the method comprising:
   locating a selected vein which is either a superior epigastric vein or a musculophrenic vein;
   establishing access to the selected vein;
   introducing a catheter into the selected vein;
   injecting a contrast agent through the catheter; and
   taking a first venography.

2. The method of claim 1, wherein the catheter comprises:
   an elongate shaft having a proximal end region and a distal end region, the elongate shaft comprising a plurality of lumens extending from the proximal end region to the distal end region;
   a first inflatable balloon coupled to the elongate shaft and in fluid communication with a first lumen of the plurality of lumens;
   a first port positioned at a distal end of the elongate shaft, the first port distal to the first inflatable balloon and in fluid communication with a second lumen of the plurality of lumens;
   a second port extending through a side wall of the elongate shaft, the second port proximal to the first inflatable balloon and in fluid communication with a third lumen of the plurality of lumens; and
   a hub assembly affixed to the elongate shaft adjacent to the proximal end region of the elongate shaft.

3. The method of claim 2, wherein the catheter further comprises:
   a second inflatable balloon coupled to the elongate shaft proximal to the first inflatable balloon and in fluid communication with the first lumen of the plurality of lumens; and
   wherein the second port is distal to the second inflatable balloon.

4. The method of claim 2, wherein the catheter has a length in the range of 30 to 50 centimeters.

5. The method of claim 2, wherein the elongate shaft has a length in the range of 20 to 40 centimeters.

6. The method of claim 2, wherein the hub assembly comprises a first injection port.

7. The method of claim 6, wherein the first injection port is in fluid communication with the second lumen.

8. The method of claim 6, wherein the hub assembly comprises a second injection port.

9. The method of claim 8, wherein the second injection port is in fluid communication with the third lumen.

10. The method of claim 2, wherein the catheter further comprises a third port extending through a side wall of the elongate shaft, the third port proximal to the second inflatable balloon and in fluid communication with a fourth lumen of the plurality of lumens.

11. The method of claim 10, wherein the hub assembly comprises a third injection port.

12. The method of claim 11, wherein the third injection port is in fluid communication with the fourth lumen.

13. The method of claim 1, further comprising choosing an implant location based on a size of the selected vein revealed by the first venography.

14. A method of implanting a lead for use in a cardiac stimulus system in a patient, the lead having at least one electrode thereon; the method comprising:
   locating a selected vein which is either a superior epigastric vein or a musculophrenic vein;
   establishing access to the selected vein;
   introducing a catheter into the selected vein;
   injecting a contrast agent through the catheter;
   taking a first venography;
   using the first venography to identify a target vein having sufficient size to at least receive the lead; and
   inserting the lead into the target vein to a desired location relative to a heart of a patient.

15. The method of claim 14 wherein the target vein is an internal thoracic vein.

16. The method of claim 14 wherein the target vein is an intercostal vein.

17. The method of claim 14 wherein the target vein is selected from the group consisting of the azygos vein, the hemiazygos vein, and the accessory hemiazygos vein.

18. A method for identifying an implant location for implanting a lead for use in a cardiac stimulus system in a patient, the lead having at least one electrode thereon; the method comprising:
   locating a selected vein which is one of a superior epigastric vein or a musculophrenic vein;
   establishing access to the selected vein;
   introducing a catheter into the selected vein;
   injecting a contrast agent through the catheter at a first location in the patient;
   taking a first venography;
   injecting the contrast agent through the catheter at a second location in the patient; and
   taking a second venography.

19. The method of claim 18, wherein the first location in the patient is adjacent to a first injection port in the catheter and the second location in the patient is adjacent to a second injection port in the catheter.

20. The method of claim 18, wherein the catheter is moved within the patient prior to injection of the contrast agent at the second location in the patient.

* * * * *